(12) United States Patent
He et al.

(10) Patent No.: US 11,661,660 B2
(45) Date of Patent: May 30, 2023

(54) METHODS FOR PRODUCING HYDROCARBON PRODUCTS AND PROTONATION PRODUCTS THROUGH ELECTROCHEMICAL ACTIVATION OF ETHANE

(71) Applicant: Battelle Energy Alliance, LLC, Idaho Falls, ID (US)

(72) Inventors: Ting He, Idaho Falls, ID (US); Dong Ding, Idaho Falls, ID (US); Yunya Zhang, Idaho Falls, ID (US); Wei Wu, Idaho Falls, ID (US); Hanping Ding, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 212 days.

(21) Appl. No.: 16/493,114

(22) PCT Filed: Mar. 15, 2018

(86) PCT No.: PCT/US2018/022615
§ 371 (c)(1),
(2) Date: Sep. 11, 2019

(87) PCT Pub. No.: WO2018/170252
PCT Pub. Date: Sep. 20, 2018

(65) Prior Publication Data
US 2020/0115808 A1   Apr. 16, 2020

Related U.S. Application Data

(60) Provisional application No. 62/472,290, filed on Mar. 16, 2017.

(51) Int. Cl.
*C25B 3/03*  (2021.01)
*C25B 3/25*  (2021.01)
(Continued)

(52) U.S. Cl.
CPC ............... *C25B 3/00* (2013.01); *C07C 11/04* (2013.01); *C25B 1/02* (2013.01); *C25B 9/19* (2021.01);
(Continued)

(58) Field of Classification Search
CPC .... C25B 3/23; C25B 3/25; C25B 3/03; C25B 3/26
(Continued)

(56) References Cited

U.S. PATENT DOCUMENTS 5,064,733 A    11/1991  Krist et al.
5,244,753 A *  9/1993   Taniguchi ........... H01M 8/1246
                                              429/488
(Continued)

FOREIGN PATENT DOCUMENTS

CN   102515750 A     6/2012
JP   2015-147998 A   8/2015
WO   2016/178948 A1  11/2016

OTHER PUBLICATIONS

Konwar et al., "A Methane-Fueled SOFC Based on a Thin BaZr0.1Ce0.7Y0.1Yb0.1O3-δ Electrolyte Film and a LaNi0.6Co0.4O3 Anode Functional Layer," Journal of Materials Chemistry A (2016), vol. 4, No. 14, pp. 5102-5106. (Year: 2016).*

(Continued)

*Primary Examiner* — Edna Wong
(74) *Attorney, Agent, or Firm* — TraskBritt

(57) ABSTRACT

A method of forming a hydrocarbon product and a protonation product comprises introducing $C_2H_6$ to a positive electrode of an electrochemical cell comprising the positive electrode, a negative electrode, and a proton-conducting membrane between the positive electrode and the negative electrode. The proton-conducting membrane comprises an electrolyte material having an ionic conductivity greater (Continued)

than or equal to about $10^{-2}$ S/cm at one or more temperatures within a range of from about 150° C. to about 650° C. A potential difference is applied between the positive electrode and the negative electrode of the electrochemical cell to produce the hydrocarbon product and the protonation product. A $C_2H_6$ activation system and an electrochemical cell are also described.

9 Claims, 5 Drawing Sheets

(51) Int. Cl.
| | |
|---|---|
| *C25B 3/26* | (2021.01) |
| *C25B 3/00* | (2021.01) |
| *C07C 11/04* | (2006.01) |
| *C25B 1/02* | (2006.01) |
| *C25B 13/04* | (2021.01) |
| *C25B 15/02* | (2021.01) |
| *C25B 9/19* | (2021.01) |
| *C25B 11/04* | (2021.01) |

(52) U.S. Cl.
CPC .............. *C25B 13/04* (2013.01); *C25B 15/02* (2013.01); *C25B 11/04* (2013.01)

(58) Field of Classification Search
USPC .......................................................... 205/462
See application file for complete search history.

(56) References Cited

U.S. PATENT DOCUMENTS

| | | | |
|---|---|---|---|
| 6,332,968 B1 | 12/2001 | Mazanec et al. | |
| 9,281,525 B2 | 3/2016 | De et al. | |
| 9,724,640 B2 | 8/2017 | Joo et al. | |
| 2005/0026006 A1 | 2/2005 | Haile et al. | |
| 2008/0283411 A1* | 11/2008 | Eastman | F02M 25/12 205/343 |
| 2008/0318094 A1 | 12/2008 | Ginosar et al. | |
| 2010/0233056 A1 | 9/2010 | Luo et al. | |
| 2011/0183221 A1 | 7/2011 | Serra et al. | |
| 2011/0262839 A1 | 10/2011 | Kang et al. | |
| 2013/0118910 A1* | 5/2013 | Teamey | C07C 51/15 205/427 |
| 2014/0272667 A1 | 9/2014 | Haile et al. | |
| 2015/0119542 A1 | 4/2015 | Weissman et al. | |
| 2016/0204444 A1 | 7/2016 | Tong et al. | |
| 2018/0363150 A1 | 12/2018 | Alvarez et al. | |
| 2019/0284048 A1* | 9/2019 | Kjølseth | C25B 9/23 |

OTHER PUBLICATIONS

Shi et al., "Protonic Membrane for Fuel Cell for Co-Generation of Power and Ethylene," Journal of Power Sources (Jan. 21, 2008), vol. 176, No. 1, pp. 122-127. (Year: 2008).*
Amar et al., "Solid-State Electrochemical Synthesis of Ammonia: A Review," Journal of Solid State Electrochemistry (Sep. 1, 2011), vol. 15, No. 9, pp. 1845-1860. (Year: 2011).*
Souza et al., "Properties and Applications of Perovskite Proton Conductors," Materials Research (Sep. 2010), vol. 13, No. 3, pp. 385-394. (Year: 2010).*
Fu et al., "Ethane Dehydrogenation over Nano-Cr2O3 Anode Catalyst in Proton Ceramic Fuel Cell Reactors to Co-Produce Ethylene and Electricity," Journal of Power Sources (Feb. 1, 2011), vol. 196, No. 3, pp. 1036-1041. (Year: 2011).*
Fu et al., "CO2 Emission Free Co-Generation of Energy and Ethylene in Hydrocarbon SOFC Reactors with a Dehydrogenation Anode," Physical Chemistry Chemical Physics (2011), vol. 13, No. 43, pp. 19615-19623. (Year: 2011).*
Chen et al., "Performance on PBI/H3PO4 Proton Conducting membrane Fuel Cell Using Ethane as Fuel," Chinese Journal of Inorganic Chemistry (Jan. 2010), vol. 26, No. 1, pp. 132-137. (Year: 2010).*
Li et al., "Evaluation of Molybdenum Carbide as Anode Catalyst for Proton-Conducting Hydrogen and Ethane Solid Oxide Fuel Cells," Electrochemistry Communications (Feb. 1, 2012), vol. 15, No. 1, pp. 81-84. (Year: 2012).*
Feng et al., "Propane Dehydrogenation in a Proton-Conducting Fuel Cell," The Journal of Physical Chemistry C (Jul. 3, 2008), vol. 112, No. 26, pp. 9943-9949. (Year: 2008).*
Lyagaeva et al., "BaCe0.5Zr0.3Y0.2-xYbxO3-o Proton-Conducting Electrolytes for Intermediate-Temperature Solid Oxide Fuel Cells ," Electrochimica Acta (Oct. 10, 2017), vol. 251, pp. 554-561. (Year: 2017).
Fabbri et al., "Design and fabrication of a chemically-stable proton conductor bilayer electrolyte for intermediate temperature solid oxide fuel cells (IT-SOFCs)", Energy & Environmental Science, vol. 1, (Jun. 2008), pp. 355-359.
Fu et al., "Ethane dehydrogenation over nano-Cr2O3 anode catalyst in proton ceramic fuel cell reactors to co-produce ethylene and electricity", Journal of Power Souices, vol. 196, Issue 3, (Aug. 2010), pp. 1036-1041.
Kim et al., "Triple-Conducting Layered Perovskites as Cathode Materials for Proton-Conducting Solid Oxide Fuel Cells", ChemSusChem, vol. 7, Issue 10, (Aug. 2014), pp. 2811-2815.
Konwar et al., "A methane-fueled SOFC based on a thin BaZr0.1Ce0.7Y0.1Yb0.1O3-electrolyte film and a LaNi0.6Co0.4O3 anode functional layer", Journal of Materials Chemistry A, vol. 4, (Mar. 2016) pp. 5102-5106.
Li et al., "BaZr0.1Ce0.7Y0.1Yb0.1O3—? as highly active and carbon tolerant anode for direct hydrocarbon solid oxide fuel cells", International Journal of Hydrogen Energy, vol. 39 (Jan. 2014) pp. 15975-15981.
Nahreen et al., "Catalytic Upgrading of Methane to Higher Hydrocarbon in a Nonoxidative Chemical Conversion", American Chemical Society, Energy & Fuels, vol. 30, (Mar. 2016) pp. 2584-2593.
Yamazaki et al., "High Total Proton Conductivity in Large-Grained Yttrium-Doped Barium Zirconate", ChemMater, vol. 21, Issue 13, (May 2009), pp. 2755-2762.
International Search Report from International Application No. PCT/US2018/002615, dated Aug. 8, 2018, 4 pages.
International Written Opinion from International Application No. PCT/US2018/002615, dated Aug. 8, 2018, 8 pages.
Matsumoto et al., "Proton-Conducting Oxide and Applications to Hydrogen Energy Devices," Pure and Applied Chemistry (Nov. 17, 2012), vol. 85, No. 2, pp. 427-435. (Year: 2012).
Wang et al., "Perovskite-Based Mixed Protonic-Electronic Conducting Membranes for Hydrogen Separation: Recent Status and Advances," Journal of Industrial and Engineering Chemistry (Apr. 25, 2018), vol. 60, pp. 297-306. (Year 2018).

* cited by examiner

METHODS FOR PRODUCING HYDROCARBON PRODUCTS AND PROTONATION PRODUCTS THROUGH ELECTROCHEMICAL ACTIVATION OF ETHANE

CROSS-REFERENCE TO RELATED APPLICATIONS

This application is a national phase entry under 35 U.S.C. § 371 of International Patent Application PCT/US2018/022615, filed Mar. 15, 2018, designating the United States of America and published as International Patent Publication WO 2018/170252 A1 on Sep. 20, 2018, which claims the benefit of the filing date under Article 8 of the Patent Cooperation Treaty to U.S. Provisional Patent Application Ser. No. 62/472,290, filed Mar. 16, 2017, for "METHODS, SYSTEMS, AND ELECTROCHEMICAL CELLS FOR PRODUCING HYDROCARBONS AND PROTONATION PRODUCTS THROUGH ELECTROCHEMICAL ACTIVATION OF ETHANE."

GOVERNMENT RIGHTS

This invention was made with government support under Contract No DE-AC07-0541314517 awarded by the United States Department of Energy. The government has certain rights in the invention.

TECHNICAL FIELD

The disclosure, in various embodiments, relates to methods, systems, and apparatuses for producing hydrocarbon products and protonation products through electrochemical activation of ethane.

BACKGROUND

Large reserves of natural gas and natural gas liquids continue to be discovered throughout the world, and have resulted in surpluses of ethane ($C_2H_6$) (i.e., the second major constituent of natural gas and natural gas liquids after methane ($CH_4$)). $C_2H_6$ is predominantly used to form ethylene ($C_2H_4$), a chemical feedstock for plastics (e.g., polyethylene) manufacturing, through conventional stream cracking processes. However, conventional stream cracking processes to convert $C_2H_6$ to $C_2H_4$ can require high temperatures (e.g., temperatures greater than or equal to about 850° C.) to activate $C_2H_6$, resulting in undesirable energy expenditures (e.g., thermal energy expenditures) and/or environmental impacts (e.g., greenhouse gas emissions effectuated by the energy needs of the stream cracking processes). In addition, conventional stream cracking processes can require the use of complicated and costly systems and methods to purify (e.g., refine) the resulting ethylene product.

It would be desirable to have new methods, systems, and apparatuses for synthesizing hydrocarbon products from $C_2H_6$. It would also be desirable if new methods, systems, and apparatuses facilitated the production of hydrocarbons other than ethylene, and also facilitated the production (e.g., co-production) and isolation of one or more protonation products. It would further be desirable if the new methods, systems, and apparatuses facilitated increased production efficiency, increased operational life, increased manufacturing flexibility, and were relatively inexpensive and simple in operation.

BRIEF SUMMARY

Embodiments described herein include methods, systems, and apparatuses for producing hydrocarbon products and protonation products (e.g., hydrogen gas ($H_{2(g)}$), $CO_2$ protonation products) through electrochemical activation of $C_2H_6$. In accordance with one embodiment described herein, a method of forming a hydrocarbon product and a protonation product comprises introducing $C_2H_6$ to a positive electrode of an electrochemical cell comprising the positive electrode, a negative electrode, and a proton-conducting membrane between the positive electrode and the negative electrode. The proton-conducting membrane comprises an electrolyte material having an ionic conductivity greater than or equal to about $10^{-2}$ S/cm at one or more temperatures within a range of from about 150° C. to about 650° C. A potential difference is applied between the positive electrode and the negative electrode of the electrochemical cell.

In additional embodiments, a $C_2H_6$ activation system comprises a source of $C_2H_6$ and an electrochemical apparatus in fluid communication with the source of $C_2H_6$. The electrochemical apparatus comprises a housing structure configured and positioned to receive a $C_2H_6$ stream from the source of $C_2H_6$, and an electrochemical cell within an internal chamber of the housing structure. The electrochemical cell comprises a positive electrode, a negative electrode, and a proton-conducting membrane between the positive electrode and the negative electrode. The positive electrode is formulated to accelerate reaction rates to produce $C_2H_4$, and $e^-$ from $C_2H_6$. The negative electrode is formulated to accelerate reaction rates to synthesize a protonation product using the produced $H^+$. The proton-conducting membrane comprises an electrolyte material having an ionic conductivity greater than or equal to about $10^{-2}$ S/cm at one or more temperatures within a range of from about 150° C. to about 650° C.

In further embodiments, an electrochemical cell comprises a positive electrode, a negative electrode, and a proton-conducting membrane between the positive electrode and the negative electrode. The positive electrode comprises a first catalyst material formulated to accelerate to $C_2H_6$ deprotonation reaction rates to produce $C_2H_4$, $H^+$, and $e^-$, from $C_2H_6$, and to accelerate ethyl coupling reaction rates to synthesize at least one hydrocarbon product from the produced $C_2H_4$. The negative electrode comprises a second catalyst material formulated to accelerate reaction rates to synthesize a protonation product using the produced $H^+$. The proton-conducting membrane comprises an electrolyte material having an ionic conductivity greater than or equal to about $10^{-2}$ S/cm at one or more temperatures within a range of from about 150° C. to about 650° C.

DETAILED DESCRIPTION

Figure 1:
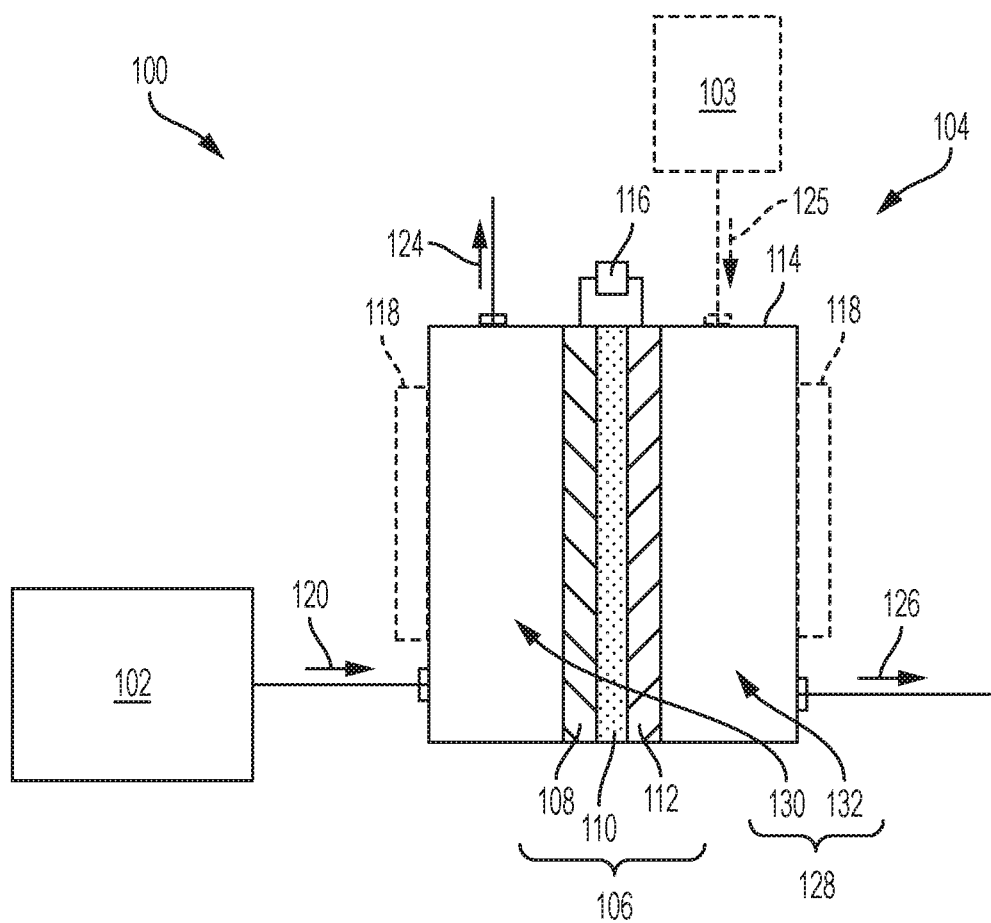
FIG. 1 is a simplified schematic view of a $C_2H_6$ activation system, in accordance with an embodiment of the disclosure.

Methods, systems, and apparatuses for producing (e.g., co-producing) hydrocarbon products and protonation products (e.g., $H_{2(g)}$, $CO_2$ protonation products) through electrochemical activation of $C_2H_6$ are disclosed. In some embodiments, a method of producing hydrocarbon products and protonation products includes directing $C_2H_6$ into an electrochemical apparatus including an electrochemical cell therein. The electrochemical cell comprises a positive electrode (anode), a negative electrode (cathode), and a proton-conducting membrane between the positive electrode and the negative electrode. The proton-conducting membrane includes an electrolyte material having an ionic conductivity greater than or equal to about $10^{-2}$ Siemens per centimeter (S/cm) at one or more temperatures within a range of from about 150° C. to about 650° C. The positive electrode includes one or more catalysts formulated to accelerate $C_2H_6$ deprotonation reaction rates to produce $C_2H_4$, $H^+$, and $e^-$ from $C_2H_6$, and may also include one or more catalysts formulated to accelerate ethyl coupling reaction rates to synthesize one or more hydrocarbon products from the produced $C_2H_4$. The negative electrode may be formulated to accelerate hydrogen evolution reaction rates to produce $H_{2(g)}$ from $H^+$ and $e^-$, and/or may be formulated to accelerate protonation reactions between $CO_2$, $e^-$, and, optionally, one or more other materials (e.g., $CO_2$ protonation products, other molecules, etc.) to produce one or more protonation products. Electrical current is applied across the positive electrode and the negative electrode of the electrochemical cell at a temperature within the range of from about 150° C. to about 650° C. to produce at least one hydrocarbon product (e.g., one or more of butylene, gasoline, and diesel) at the positive electrode and at least one protonation product at the negative electrode. The methods, systems, and apparatuses of the disclosure may be more efficient (e.g., increasing production efficiency; reducing equipment, material, and/or energy requirements; etc.), more durable, and/or less complicated as compared to conventional methods, conventional systems, and conventional apparatuses.

The following description provides specific details, such as material compositions and processing conditions (e.g., temperatures, pressures, flow rates, etc.) in order to provide a thorough description of embodiments of the disclosure. However, a person of ordinary skill in the art will understand that the embodiments of the disclosure may be practiced without necessarily employing these specific details. Indeed, the embodiments of the disclosure may be practiced in conjunction with conventional systems and methods employed in the industry. In addition, only those process components and acts necessary to understand the embodiments of the present disclosure are described in detail below. A person of ordinary skill in the art will understand that some process components (e.g., pipelines, line filters, valves, temperature detectors, flow detectors, pressure detectors, and the like) are inherently disclosed herein and that adding various conventional process components and acts would be in accord with the disclosure. In addition, the drawings accompanying the disclosure are for illustrative purposes only, and are not meant to be actual views of any particular material, device, or system.

As used herein, the term "lower hydrocarbon" means and includes an aliphatic hydrocarbon having from one carbon atom to four carbon atoms (e.g., methane, ethane, ethylene, acetylene, propane, propylene, n-butane, isobutane, butane, isobutene, etc.).

As used herein, the terms "higher hydrocarbon" and "hydrocarbon product" mean and include an aliphatic or cyclic hydrocarbon having at least one more carbon atom than a lower hydrocarbon used to form the higher hydrocarbon.

As used herein, the term "cyclic hydrocarbon" means and includes at least one closed ring hydrocarbon, such as an alicyclic hydrocarbon, an aromatic hydrocarbon, or a combination thereof. The cyclic hydrocarbon may include only carbon and hydrogen, or may include carbon, hydrogen, and at least one heteroatom.

As used herein, the term "heteroatom" means and includes an element other than carbon and hydrogen, such as oxygen (O), nitrogen (N), or sulfur (S).

As used herein, the terms "catalyst material" and "catalyst" each mean and include a material formulated to promote one or more reactions, resulting in the formation of a product.

As used herein, the term "negative electrode" means and includes an electrode having a relatively lower electrode potential in an electrochemical cell (i.e., lower than the electrode potential in a positive electrode therein). Conversely, as used herein, the term "positive electrode" means and includes an electrode having a relatively higher electrode potential in an electrochemical cell (i.e., higher than the electrode potential in a negative electrode therein).

As used herein the term "electrolyte" means and includes an ionic conductor, which can be in a solid state, a liquid state, or a gas state (e.g., plasma).

As used herein, spatially relative terms, such as "beneath," "below," "lower," "bottom," "above," "upper," "top," "front," "rear," "left," "right," and the like, may be used for ease of description to describe one element's or feature's relationship to another element(s) or feature(s) as illustrated in the figures. Unless otherwise specified, the spatially relative terms are intended to encompass different orientations of the materials in addition to the orientation depicted in the figures. For example, if materials in the figures are inverted, elements described as "below" or "beneath" or "under" or "on bottom of" other elements or features would then be oriented "above" or "on top of" the other elements or features. Thus, the term "below" can encompass both an orientation of above and below, depending on the context in which the term is used, which will be evident to one of ordinary skill in the art. The materials may be otherwise oriented (e.g., rotated 90 degrees, inverted, flipped) and the spatially relative descriptors used herein interpreted accordingly.

As used herein, the singular forms "a," "an," and "the" are intended to include the plural forms as well, unless the context clearly indicates otherwise.

As used herein, "and/or" includes any and all combinations of one or more of the associated listed items.

As used herein, the term "configured" refers to a size, shape, material composition, material distribution, and arrangement of one or more of at least one structure and at least one apparatus facilitating operation of one or more of the structure and the apparatus in a pre-determined way.

As used herein, the term "substantially" in reference to a given parameter, property, or condition means and includes to a degree that one of ordinary skill in the art would understand that the given parameter, property, or condition is met with a degree of variance, such as within acceptable tolerances. By way of example, depending on the particular parameter, property, or condition that is substantially met, the parameter, property, or condition may be at least 90.0 percent met, at least 95.0 percent met, at least 99.0 percent met, at least 99.9 percent met, or even 100.0 percent met.

As used herein, the term "about" or "approximately" in reference to a numerical value for a particular parameter is inclusive of the numerical value and a degree of variance from the numerical value that one of ordinary skill in the art would understand is within acceptable tolerances for the particular parameter. For example, "about" or "approximately" in reference to a numerical value may include additional numerical values within a range of from 90.0 percent to 110.0 percent of the numerical value, such as within a range of from 95.0 percent to 105.0 percent of the numerical value, within a range of from 97.5 percent to 102.5 percent of the numerical value, within a range of from 99.0 percent to 101.0 percent of the numerical value, within a range of from 99.5 percent to 100.5 percent of the numerical value, or within a range of from 99.9 percent to 100.1 percent of the numerical value.

As used herein, the term "compatible" means that a material does not undesirably react, decompose, or absorb another material, and also that the material does not undesirably impair the chemical and/or mechanical properties of the another material.

An embodiment of the disclosure will now be described with reference to FIG. 1, which schematically illustrates a $C_2H_6$ activation system 100. The $C_2H_6$ activation system 100 may be used to convert $C_2H_6$ into at least one other hydrocarbon (e.g., at least one higher hydrocarbon, such as butylene, gasoline, diesel, etc.), and may also be used to produce one or more protonation products (e.g., $H_{2(g)}$, $CO_2$ protonation products) using hydrogen ions ($H^+$) (i.e., protons) removed from the $C_2H_6$. As shown in FIG. 1, the $C_2H_6$ activation system 100 may include at least one $C_2H_6$ source 102 (e.g., containment vessel), and at least one electrochemical apparatus 104 in fluid communication with the $C_2H_6$ source 102. The electrochemical apparatus 104 includes a housing structure 114, and at least one electrochemical cell 106 contained within the housing structure 114. The electrochemical cell 106 is electrically connected (e.g., coupled) to a power source 116, and includes a positive electrode 108, a negative electrode 112, and a proton-conducting membrane 110 between the positive electrode 108 and the negative electrode 112. As shown in FIG. 1, optionally, the $C_2H_6$ activation system 100 may also include at least one $CO_2$ source 103 (e.g., containment vessel) in fluid communication with the electrochemical apparatus 104. In addition, as also shown in FIG. 1, optionally, the $C_2H_6$ activation system 100 may include at least one heating apparatus 118 operatively associated with the electrochemical apparatus 104.

During use and operation, the $C_2H_6$ activation system 100 directs a $C_2H_6$ stream 120 into the electrochemical apparatus 104 to interact with the positive electrode 108 of the electrochemical cell 106. A potential difference (e.g., voltage) is applied between the positive electrode 108 and the negative electrode 112 of the electrochemical cell 106 by the power source 116 so that as the $C_2H_6$ interacts with the positive electrode 108, H atoms of the $C_2H_6$ release their electrons (e) to generate ethylene ($C_2H_4$), $H^+$, and $e^-$ through non-oxidative deprotonation according to the following equation:

$$C_2H_6 \rightarrow C_2H_4 + 2H^+ + 2e^- \quad (1).$$

The generated $H^+$ permeate (e.g., diffuse) across the proton-conducting membrane 110 to the negative electrode 112, and the generated $e^-$ are directed to the power source 116 through external circuitry. Depending on the material composition of the positive electrode 108, the produced $C_2H_4$ may undergo at least one ethyl coupling reaction in the presence of one or more catalysts of the positive electrode 108 to synthesize at least one hydrocarbon product (e.g., at least one higher hydrocarbon), according to the following equation:

$$nC_2H_4 \rightarrow C_{2n}H_{4n} \quad (2).$$

Hydrocarbons (e.g., $C_2H_4$, higher hydrocarbons) produced at the positive electrode 108 exit the electrochemical apparatus 104 as a hydrocarbon product stream 124.

At the negative electrode 112, if the $CO_2$ source 103 is absent (e.g., omitted) from the $C_2H_6$ activation system 100, generated $H^+$ exiting the proton-conducting membrane 110 react with $e^-$ received from the power source 116 to form H atoms that the combine to form $H_{2(g)}$ through a hydrogen evolution reaction, according to the following equation:

$$4H^+ + 4e^- \rightarrow 2H_{2(g)} \quad (3)$$

However, if the $C_2H_6$ activation system 100 includes the $CO_2$ source 103, generated $H^+$ exiting the proton-conducting membrane 110 react with $CO_2$ delivered into the electrochemical apparatus 104 from a $CO_2$ stream 125 directed from the $CO_2$ source 103, $e^-$ received from the power source 116, and, optionally, one or more other materials (e.g., $CO_2$ protonation products previously formed through reactions between $H^+$, $e^-$, and one or more of $CO_2$ and other $CO_2$ protonation products; reaction products of $CO_2$ and one or more of $CO_2$ protonation products and other molecules delivered to the negative electrode 112 side of the electrochemical cell 106; etc.) to form one or more other products (e.g., one or more of an alcohol, an aldehyde, a carboxylic acid, a formate, a methylated amine, formaldehyde, formic acid, a formamide, etc.). As a non-limiting example, at the negative electrode 112, $CO_2$ from the $CO_2$ stream 125 (if any) may react with generated $H^+$ exiting the proton-conducting membrane 110 and $e^-$ received from the power source 116 to produce formic acid according to the following equation:

$$CO_2^{2-} \xrightarrow{2H^+, 2e^-} CH_2O_2. \quad (4)$$

As another non-limiting example, formic acid produced at the negative electrode 112 according to the reaction of Equation (4) above may react with additional generated $H^+$ exiting the proton-conducting membrane 110 and additional $e^-$ received from the power source 116 to produce formaldehyde according to the following equation:

$$CH_2O_2 \xrightarrow[-H_2O]{2H^+, 2e^-} CH_2O. \quad (5)$$

As a further non-limiting example, formaldehyde produced at the negative electrode 112 according to the reaction of Equation (5) above may directly react with yet additional generated $H^+$ exiting the proton-conducting membrane 110 and yet additional e⁻ received from the power source 116 to produce methanol according to the following equation:

(6)

Of course, it will be readily apparent to one of ordinary skill in the art that a wide variety of products (e.g., beyond formic acid, formaldehyde, and methanol) may be formed through protonation of one or more of $CO_2$, $CO_2$ protonation products, and derivatives of $CO_2$ protonation products at the negative electrode 112. By way of non-limiting example, the $C_2H_6$ activation system 100 may be used to form one or more of formic acid, formaldehyde, methanol, a formate, a methylated amine, an alcohol other than methanol, a carboxylic acid, a formamide, and an aldehyde, which have the general structures shown below:

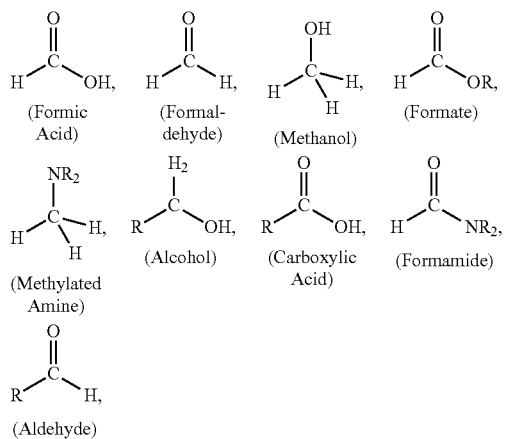

where each R may individually be hydrogen; a substituted or unsubstituted alkyl group (e.g., linear, branched, or cyclic) containing from 1 carbon atom to 10 carbon atoms; or a substituted or unsubstituted aryl group or heteroaryl group. If a group is substituted, the substituent may be an alkyl, alkenyl, alkynl, alkyl halide, aryl, aryl halide, heteroaryl, non-aromatic ring, Si(alkyl)₃, Si(alkoxy)₃, alkoxy, amino, ester, amide, thioether, alkylcarbonate, or thioester group. Additional protonation products (e.g., methane ($CH_4$), acetylene ($C_2H_2$)) may also be synthesized through reactions between $CO_2$ from the $CO_2$ stream 125, the generated $H^+$ exiting the proton-conducting membrane 110, and the e⁻ received from the power source 116. Protonation products (e.g., $H_{2(g)}$, formic acid, formaldehyde, methanol, formates, methylated amines, alcohols other than methanol, carboxylic acids, formamides, aldehydes, etc.) produced at the negative electrode 112 exit the electrochemical apparatus 104 as a protonation product stream 126.

Figure 2:
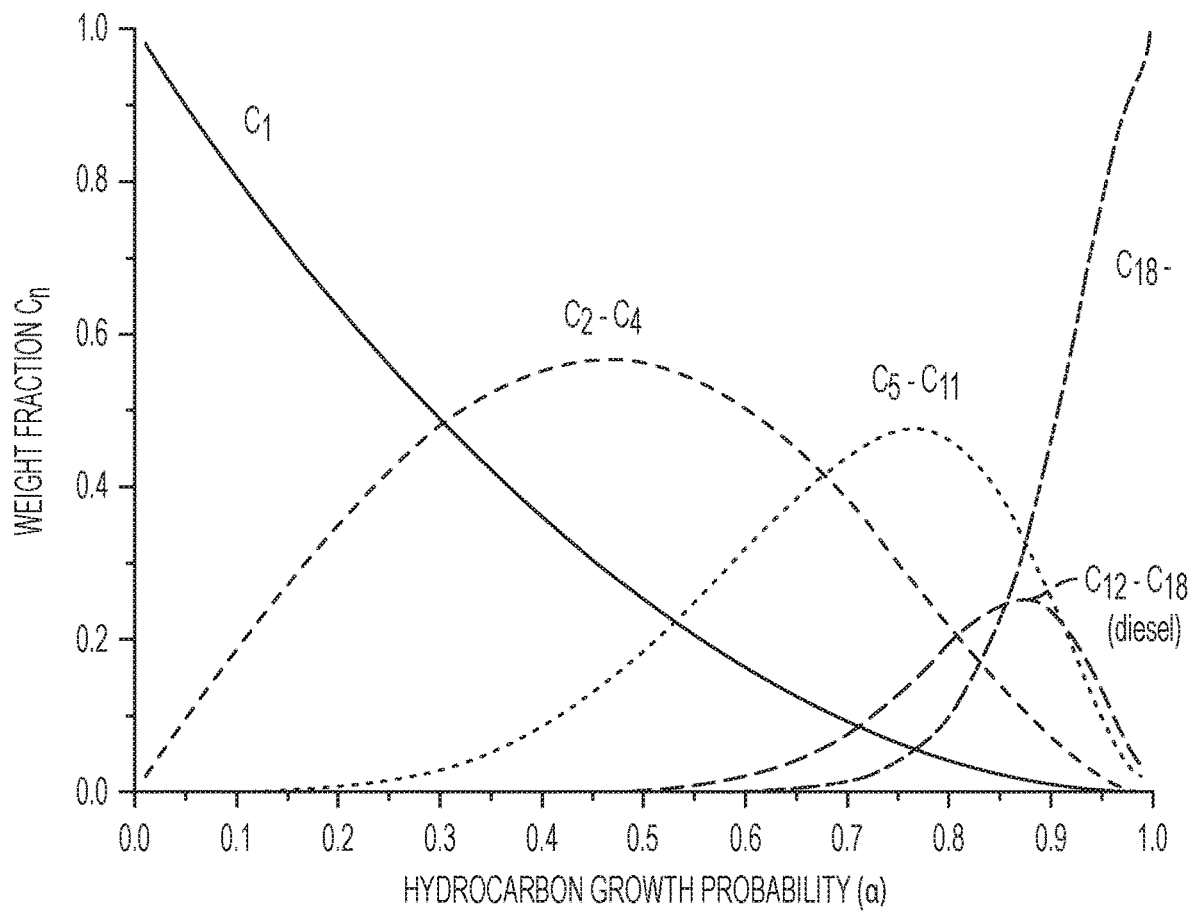
FIG. 2 is a graph of a mathematically modeled Anderson-Schulz-Flory distribution.

As described in further detail below, the hydrocarbon products synthesized at the positive electrode 108 and the protonation products synthesized at the negative electrode 112 may at least partially depend on the material composition and flow rate of the $C_2H_6$ stream 120; the configuration (e.g., size, shape, material composition, material distribution, arrangement) of the positive electrode 108, including the types, quantities, distribution, and properties (e.g., geometric properties, thermodynamic properties, etc.) of catalysts thereof promoting $C_2H_6$ deprotonation reactions and/or ethyl coupling reactions; the configuration of the proton-conducting membrane 110, and the impact thereof on the diffusivity (e.g., diffusion rate) of generated $H^+$ therethrough; the configuration of the negative electrode 112, including the types, quantities, and properties (e.g., geometric properties, thermodynamic properties, etc.) of catalysts thereof; the material composition and flow rate of the $CO_2$ stream 125 (if any); and the operational parameters (e.g., temperatures, pressures, etc.) of the electrochemical apparatus 104. Such operational factors may be controlled (e.g., adjusted, maintained, etc.) as desired to control the types, quantities, and rate of production of the hydrocarbon product(s) synthesized at the positive electrode 108 and to control the types, quantities, and rate of production of the protonation product(s) synthesized at the negative electrode 112. In some embodiments, the hydrocarbon product(s) exiting the electrochemical apparatus 104 in the hydrocarbon product stream 124 may be examined (e.g., through in-line gas chromatography-mass spectrometry (GS-MS)) and compared to a mathematically modeled Anderson-Schulz-Flory distribution, such as that illustrated in FIG. 2, to analyze whether or not sufficient ethyl coupling reactions are occurring at the positive electrode 108 for the synthesis of one or more desired higher hydrocarbons. One or more operational factors of the $C_2H_6$ activation system 100 (e.g., one or more of the type, quantity, and distribution of catalyst material(s) in the positive electrode 108, the operating temperature of the electrochemical apparatus 104, etc.) may be adjusted or maintained based on the results of the analysis. Accordingly, the operational factors of the $C_2H_6$ activation system 100 may be tailored to facilitate the production of one or more specific higher hydrocarbons from the components (e.g., $C_2H_6$) of the $C_2H_6$ stream 120.

The $C_2H_6$ stream 120 may be formed on and include $C_2H_6$. In addition, the $C_2H_6$ stream 120 may, optionally, include one or more other materials (e.g., molecules), such as one or more other lower hydrocarbons (e.g., one or more other $C_1$ to $C_4$ hydrocarbons, such as one or more of methane, propane, and butane) that may undergo a chemical reaction in the presence of the positive electrode 108 of the electrochemical cell 106 to produce at least one higher hydrocarbon, and/or one or more other materials (e.g., $H_2$, nitrogen ($N_2$), etc.). In some embodiments, the $C_2H_6$ stream 120 is substantially free of materials other than $C_2H_6$. In additional embodiments, the $C_2H_6$ stream 120 includes $C_2H_6$ and $CH_4$. The $C_2H_6$ stream 120 may be substantially gaseous (e.g., may only include a single gaseous phase), may be substantially liquid (e.g., may only include a single liquid phase), or may include a combination of liquid and gaseous phases. The phase(s) of the $C_2H_6$ stream 120 (and, hence, a temperature and a pressure of the $C_2H_6$ stream 120) may at least partially depend on the operating temperature of the electrochemical cell 106 of the electrochemical apparatus 104. In some embodiments, the $C_2H_6$ stream 120 is substantially gaseous.

A single (e.g., only one) $C_2H_6$ stream 120 may be directed into the electrochemical apparatus 104 from the $C_2H_6$ source 102, or multiple (e.g., more than one) $C_2H_6$ streams 120 may be directed into the electrochemical apparatus 104 from the $C_2H_6$ source 102. If multiple $C_2H_6$ streams 120 are directed into the electrochemical apparatus 104, each of the multiple $C_2H_6$ streams 120 may exhibit substantially the same properties (e.g., substantially the same material composition, substantially the same temperature, substantially the same pressure, substantially the same flow rate, etc.), or at least one of the multiple $C_2H_6$ streams 120 may exhibit one or more different properties (e.g., a different material composition, a different temperature, a different pressure, a different flow rate, etc.) than at least one other of the multiple $C_2H_6$ streams 120.

The $CO_2$ stream 125 (if any) entering the electrochemical apparatus 104 may be formed of and include $CO_2$. The $CO_2$ may be present in the $CO_2$ stream 125 in one or more of a gaseous phase and a liquid phase. The phase(s) of the $CO_2$ (and, hence, a temperature and a pressure of the $CO_2$ stream 125) may at least partially depend on the operating temperature of the electrochemical cell 106 of the electrochemical apparatus 104. For example, at operating temperatures less than or equal to about 250° C. (e.g., within a range of from about 150° C. to about 250° C.), the $CO_2$ may be present in the $CO_2$ stream 125 in a liquid phase (e.g., $CO_2$ dissolved in an ionic liquid), a gaseous phase, or combination thereof. As another example, at operating temperatures greater than about 250° C. (e.g., greater than about 250° C. and less than or equal to about 650°), the $CO_2$ may be present in the $CO_2$ stream 125 in a gaseous phase. The $CO_2$ stream 125 may only include $CO_2$, or may include $CO_2$ and one or more other materials (e.g., inert materials; materials to be reacted with $CO_2$ protonation products to form desired products; etc.). In some embodiments, the $CO_2$ stream 125 is substantially free of materials other than $CO_2$. One or more apparatuses (e.g., heat exchangers, pumps, compressors, expanders, mass flow control devices, etc.) may be employed within the $C_2H_6$ activation system 100 to adjust the one or more of the temperature, pressure, and flow rate of the $CO_2$ stream 125 delivered into the electrochemical apparatus 104.

A single (e.g., only one) $CO_2$ stream 125 may be directed into the electrochemical apparatus 104, multiple (e.g., more than one) $CO_2$ streams 125 may be directed into the electrochemical apparatus 104, or no $CO_2$ streams 125 may be directed into the electrochemical apparatus 104. If multiple $CO_2$ streams 125 are directed into the electrochemical apparatus 104, each of the multiple $CO_2$ streams 125 may exhibit substantially the same properties (e.g., substantially the same material composition, substantially the same temperature, substantially the same pressure, substantially the same flow rate, etc.), or at least one of the multiple $CO_2$ streams 125 may exhibit one or more different properties (e.g., a different material composition, a different temperature, a different pressure, a different flow rate, etc.) than at least one other of the multiple $CO_2$ streams 125.

The heating apparatus 118, if present, may comprise at least one apparatus (e.g., one or more of a combustion heater, an electrical resistance heater, an inductive heater, and an electromagnetic heater) configured and operated to heat one or more of the $C_2H_6$ streams 120, and at least a portion of the electrochemical apparatus 104 to an operating temperature of the electrochemical apparatus 104. The operating temperature of the electrochemical apparatus 104 may at least partially depend on a material composition of the proton-conducting membrane 110 of the electrochemical cell 106 thereof, as described in further detail below. In some embodiments, the heating apparatus 118 heats one or more of the $C_2H_6$ streams 120, the $CO_2$ stream 125 (if any), and at least a portion of the electrochemical apparatus 104 to a temperature within a range of from about 150° C. to about 650° C. In additional embodiments, such as in embodiments wherein a temperature of the $C_2H_6$ stream 120 is already within the operating temperature range of the electrochemical cell 106 of the electrochemical apparatus 104, the heating apparatus 118 may be omitted (e.g., absent) from the $C_2H_6$ activation system 100.

With continued reference to FIG. 1, the electrochemical apparatus 104, including the housing structure 114 and the electrochemical cell 106 thereof, is configured and operated to form the hydrocarbon product stream 124 according to the reaction(s) of one or more of Equations (1) and (2) above, and is also configured and operated to form the protonation product stream 126 according to the reaction(s) of one or more of Equations (3) through (6) above. The housing structure 114 may exhibit any shape (e.g., a tubular shape, a quadrilateral shape, a spherical shape, a semi-spherical shape, a cylindrical shape, a semi-cylindrical shape, truncated versions thereof, or an irregular shape) and size able to contain (e.g., hold) the electrochemical cell 106 therein, to receive and direct the $C_2H_6$ stream 120 to the positive electrode 108 of the electrochemical cell 106, to direct the hydrocarbon product(s) synthesized at the positive electrode 108 away from the electrochemical apparatus 104 as the hydrocarbon product stream 124, to optionally receive and direct the $CO_2$ stream 125 (if any) to the negative electrode 112 of the electrochemical cell 106, and to direct protonation products formed at the negative electrode 112 of the electrochemical cell 106 away from the electrochemical apparatus 104 as the protonation product stream 126. In addition, the housing structure 114 may be formed of and include any material (e.g., glass, metal, alloy, polymer, ceramic, composite, combination thereof, etc.) compatible with the operating conditions (e.g., temperatures, pressures, etc.) of the electrochemical apparatus 104.

The housing structure 114 may at least partially define at least one internal chamber 128 at least partially surrounding the electrochemical cell 106. The electrochemical cell 106 may serve as a boundary between a first region 130 (e.g., an anodic region) of the internal chamber 128 configured and positioned to receive the $C_2H_6$ stream 120 and to direct the hydrocarbon product stream 124 from the electrochemical apparatus 104, and a second region 132 (e.g., a cathodic region) of the internal chamber 128 configured and positioned to receive the $CO_2$ stream 125 (if any) and to direct the protonation product stream 126 from the electrochemical apparatus 104. Molecules (e.g., $C_2H_6$) of the $C_2H_6$ stream 120 may be substantially limited to the first region 130 of the internal chamber 128 by the configurations and positions of the housing structure 114 and the electrochemical cell 106. Keeping the second region 132 of the internal chamber 128 substantially free of molecules from the $C_2H_6$ stream 120 circumvents additional processing of the protonation product(s) formed at the negative electrode 112 (e.g., to separate the protonation product(s) from $C_2H_6$) that may otherwise be necessary if the components of the $C_2H_6$ stream 120 were also delivered to within the second region 132 of the internal chamber 128.

As shown in FIG. 1, the positive electrode 108 and the negative electrode 112 of the electrochemical cell 106 are electrically coupled to a power source 116, and the proton-conducting membrane 110 is disposed on and between the positive electrode 108 and the negative electrode 112. The proton-conducting membrane 110 is configured and formulated to conduct $H^+$ from the positive electrode 108 to the negative electrode 112, while electrically insulating the negative electrode 112 from the positive electrode 108 and preventing the migration of molecules (e.g., $C_2H_6$) therethrough. Electrons generated at the positive electrode 108 through the reaction of Equation (1) described above may, for example, flow from the positive electrode 108 into a negative current collector, through the power source 116 and a positive electrode current collector, and into the negative electrode 112 to facilitate the production of protonation products (e.g., $H_{2(g)}$, $CO_2$ protonation products) through the reaction(s) of one of more of Equations (3) through (6) described above.

The proton-conducting membrane 110 may be formed of and include at least one electrolyte material exhibiting an ionic conductivity (e.g., $H^+$ conductivity) greater than or equal to about $10^{-2}$ S/cm (e.g., within a range of from about $10^{-2}$ S/cm to about 1 S/cm) at one or more temperatures within a range of from about 150° C. to about 650° C. (e.g., from about 200° C. to about 600° C.). In addition, the electrolyte material may be formulated to remain substantially adhered (e.g., laminated) to the positive electrode 108 and the negative electrode 112 at relatively high current densities, such as at current densities greater than or equal to about 0.1 amperes per square centimeter ($A/cm^2$) (e.g., greater than or equal to about 0.5 $A/cm^2$, greater than or equal to about 1.0 $A/cm^2$, greater than or equal to about 2.0 $A/cm^2$, etc.). For example, the proton-conducting membrane 110 may comprise one or more of a perovskite material, a solid acid material, and a polybenzimidazole (PBI) material. The material composition of the proton-conducting membrane 110 may provide the proton-conducting membrane 110 with enhanced ionic conductivity at a temperature within a range of from about 150° C. to about 650° C. as compared to conventional membranes (e.g., membranes employing conventional electrolyte materials, such as yttria-stabilized zirconia (YSZ)) of conventional electrochemical cells. By way of non-limiting example, the electrolyte material (e.g., perovskite material, solid acid material, PBI material) of the proton-conducting membrane 110 may have orders of magnitude higher ionic conductivity than YSZ at operational temperatures thereof within a range of from about 150° C. to about 650° C.

In some embodiments, the proton-conducting membrane 110 is formed of and includes at least one perovskite material having an operational temperature (e.g., a temperature at which the $H^+$ conductivity of the perovskite material is greater than or equal to about $10^{-2}$ S/cm, such as within a range of from about $10^{-2}$ S/cm to about $10^{-1}$ S/cm) within a range of from about 350° C. to about 650° C. By way of non-limiting example, the proton-conducting membrane 110 may comprise one or more of a yttrium- and ytterbium-doped barium-zirconate-cerate (BZCYYb), such as $BaZr_{0.8-y}Ce_yY_{0.2-x}Yb_xO_{3-\delta}$, wherein x and y are dopant levels and $\delta$ is the oxygen deficit (e.g., $BaZr_{0.3}Ce_{0.5}Y_{0.1}Yb_{0.1}O_{3-\delta}$); a yttrium- and ytterbium-doped barium-strontium-niobate (BSNYYb), such as $Ba_3(Sr_{1-x}Nb_{2-y}Y_xYb_y)O_{9-\delta}$, wherein x and y are dopant levels and $\delta$ is the oxygen deficit; doped barium-cerate ($BaCeO_3$) (e.g., yttrium-doped $BaCeO_3$ (BCY)); doped barium-zirconate ($BaZrO_3$) (e.g., yttrium-doped $BaZrO_3$ (BZY)); barium-yttrium-stannate ($Ba_2(YSn)O_{5.5}$); and barium-calcium-niobate ($Ba_3(CaNb_2)O_9$). In some embodiments, the proton-conducting membrane 110 comprises BZCYYb.

In further embodiments, the proton-conducting membrane 110 is formed of and includes at least one solid acid material having an operational temperature (e.g., a temperature at which the $H^+$ conductivity of the solid acid material is greater than or equal to about $10^{-2}$ S/cm, such as within a range of from about $10^{-2}$ S/cm to about 1 S/cm) within a range of from about 200° C. to about 400° C. By way of non-limiting example, the proton-conducting membrane 110 may comprise a solid acid phosphate material, such as solid acid cesium dihydrogen phosphate ($CsH_2PO_4$). The solid acid material may be doped (e.g., doped $CsH_2PO_4$), or may be undoped (e.g., undoped $CsH_2PO_4$). In some embodiments, the proton-conducting membrane 110 comprises $CsH_2PO_4$.

In additional embodiments, the proton-conducting membrane 110 is formed of and includes at least one PBI material having an operational temperature (e.g., a temperature at which the $H^+$ conductivity of the PBI material is greater than or equal to about $10^{-2}$ S/cm, such as within a range of from about $10^{-2}$ S/cm to about 1 S/cm) within a range of from about 150° C. to about 250° C. By way of non-limiting example, the proton-conducting membrane 110 may comprise a doped PBI, such as phosphoric acid ($H_3PO_4$) doped PBI. In some embodiments, the proton-conducting membrane 110 comprises $H_3PO_4$-doped PBI.

The proton-conducting membrane 110 may be substantially homogeneous or may be substantially heterogeneous. As used herein, the term "homogeneous" means amounts of a material do not vary throughout different portions (e.g., different lateral and longitudinal portions) of a structure. Conversely, as used herein, the term "heterogeneous" means amounts of a material vary throughout different portions of a structure. Amounts of the material may vary stepwise (e.g., change abruptly), or may vary continuously (e.g., change progressively, such as linearly, parabolically) throughout different portions of the structure. In some embodiments, the proton-conducting membrane 110 is substantially homogeneous. In additional embodiments, the proton-conducting membrane 110 is heterogeneous. The proton-conducting membrane 110 may, for example, be formed of and include a stack of at least two (e.g., at least three, at least four, etc.) different materials. As a non-limiting example, the proton-conducting membrane 110 may comprise a stack of at least two (e.g., at least three, at least four, etc.) different perovskite materials individually having an operational temperature within a range of from about 350° C. to about 650° C. As another non-limiting example, the proton-conducting membrane 110 may comprise a stack of at least two (e.g., at least three, at least four, etc.) different solid acid materials individually having an operational temperature within a range of from about 200° C. to about 400° C. As a further non-limiting example, the proton-conducting membrane 110 may comprise a stack of at least two (e.g., at least three, at least four, etc.) different PBI materials individually having an operational temperature within a range of from about 150° C. to about 250° C.

The proton-conducting membrane 110 may exhibit any desired dimensions (e.g., length, width, thickness) and any desired shape (e.g., a cubic shape, cuboidal shape, a tubular shape, a tubular spiral shape, a spherical shape, a semi-spherical shape, a cylindrical shape, a semi-cylindrical shape, a conical shape, a triangular prismatic shape, a truncated version of one or more of the foregoing, and irregular shape). The dimensions and the shape of the proton-conducting membrane 110 may be selected such that the proton-conducting membrane 110 substantially intervenes between opposing surfaces of the positive electrode 108 and the negative electrode 112, and exhibits an $H^+$ conductivity greater than or equal to about $10^{-2}$ S/cm (e.g., from about $10^{-2}$ S/cm to about 1 S/cm) at a temperature within a range of from about 150° C. to about 650° C. A thickness of the proton-conducting membrane 110 may be within a range of from about 5 micrometers (μm) to about 1000 μm, and may at least partially depend on the material composition of the proton-conducting membrane 110. For example, a proton-conducting membrane 110 formed of and including at least one perovskite material may have a thickness with a range of from about 5 μm to about 1000 μm;

a proton-conducting membrane 110 formed of and including at least one solid acid material may have a thickness with a range of from about 5 μm to about 1000 μm; and a proton-conducting membrane 110 formed of and including at least one PBI material may have a thickness with a range of from about 50 μm to about 1000 μm.

The positive electrode 108 and the negative electrode 112 may individually be formed of and include at least one material compatible with the material composition of the proton-conducting membrane 110 and the operating conditions (e.g., temperature, pressure, current density, etc.) of the electrochemical cell 106, and facilitating the formation of the hydrocarbon product stream 124 and the protonation product stream 126 from at least the $C_2H_6$ stream 120 (and the $CO_2$ stream 125 (if any)) at an operational temperature within a range of from about 150° C. to about 650° C. according to the reaction(s) of one or more of Equations (1) and (2) described above, and the reaction(s) of one or more of Equations (3) through (6) described above. Accordingly, the material compositions of the positive electrode 108 and the negative electrode 112 may be selected relative to one another, the material composition of the proton-conducting membrane 110, the material composition of the $C_2H_6$ stream 120, the material composition of the $CO_2$ stream 125 (if any), and the operating conditions of the electrochemical cell 106.

The material of the positive electrode 108 is formulated to promote the production of $C_2H_4$, $H^+$, and $e^-$ from $C_2H_6$ in accordance with Equation (1) above. For example, the material of the positive electrode 108 may comprise a catalyst-doped material including at least one catalyst thereon, thereover, and/or therein that accelerates reaction rates at the positive electrode 108 to produce $C_2H_4$, $H^+$, and $e^-$, from $C_2H_6$ in accordance with Equation (1) above. The catalyst may, for example, comprise at least one metal catalyst, such as nickel (Ni). In addition, the material of the positive electrode 108 may also be formulated to promote the synthesis of higher hydrocarbons from the produced $C_2H_4$ in accordance with Equation (2) above. For example, the material of the positive electrode 108 may comprise a catalyst-doped material that also includes at least one additional catalyst thereon, thereover, and/or therein that accelerates reaction rates at the positive electrode 108 to synthesize higher hydrocarbons from the produced $C_2H_4$ in accordance with Equation (2) above. The additional catalyst may, for example, comprise at least one additional metal catalyst, such as one or more of gold (Au), iron (Fe), zinc (Zn), molybdenum (Mo), platinum (Pt), and lead (Pb). The material of the positive electrode 108 may include particles of the catalyst (e.g., metal catalyst) and the additional catalyst (e.g., additional metal catalyst) (if any). If the material of the positive electrode 108 includes the metal catalyst (e.g., Ni) and the additional metal catalyst (e.g., Au, Fe, Zn, Mo, Pt, Pb), the positive electrode 108 may include elemental particles of the metal catalyst and additional elemental particles of the additional metal catalyst discrete from the elemental particles of the metal catalyst; may comprise alloy particles individually including an alloy of the metal catalyst and the additional metal catalyst; and/or may comprise composite particles including one of the metal catalyst and the additional metal catalyst partially (e.g., less than completely) coating (e.g., covering, encapsulating) the other of the metal catalyst and the additional metal catalyst, such as composite particles individually including a shell of the additional metal catalyst partially coating a core of the metal catalyst, and/or composite particles individually including a shell of the metal catalyst partially coating a core of the additional metal catalyst. Catalytic particles (e.g., elemental particles, alloy particles, composite particles) of the positive electrode 108 may be nano-sized (e.g., having a cross-sectional width or diameter less than about one (1) μm, such as less than or equal to about 100 nanometers (nm), less than or equal to about 20 nm, or less than or equal to about 10 nm). In addition, the positive electrode 108 may exhibit any amount (e.g., concentration) and distribution of the catalyst(s) (e.g., the catalyst, the additional catalyst) thereof, and any catalyst ratios (e.g., of the catalyst to the additional catalyst) facilitating desired $C_2H_6$ deprotonation reaction rates and desired ethyl coupling reaction rates at the positive electrode 108.

As a non-limiting example, if the proton-conducting membrane 110 comprises a perovskite material (e.g., a BZCYYb, a BSNYYb, a doped $BaCeO_3$, a doped $BaZrO_3$, $Ba_2(YSn)O_{5.5}$, $Ba_3(CaNb_2)O_9$, etc.) having an operational temperature within a range of from about 350° C. to about 650° C., the positive electrode 108 may comprise a compatible perovskite material, such as a cermet material including at least one perovskite (e.g., a BZCYYb, a BSNYYb, a doped $BaCeO_3$, a doped $BaZrO_3$, $Ba_2(YSn)O_{5.5}$, $Ba_3(CaNb_2)O_9$, etc.), at least one catalyst (e.g., at least one metal catalyst, such as Ni) formulated to promote the production of $C_2H_4$, $H^+$, and $e^-$ from $C_2H_6$ in accordance with Equation (1) above, and, optionally, at least one additional catalyst (e.g., at least one additional metal catalyst, such as one or more of Au, Fe, Zn, Mo, Pt, and Pb) formulated to promote the synthesis of higher hydrocarbons from the produced $C_2H_4$ in accordance with Equation (2) above. The positive electrode 108 may, for example, comprise one or more of a Ni/perovskite cermet (Ni-perovskite) material (e.g., Ni—BZCYYb, Ni—BSNYYb, Ni—$BaCeO_3$, Ni—$BaZrO_3$, Ni—$Ba_2(YSn)O_{5.5}$, Ni—$Ba_3(CaNb_2)O_9$); and an NiX/perovskite cermet (NiX-perovskite) material (e.g., NiX—BZCYYb, NiX—BSNYYb, NiX—$BaCeO_3$, NiX—$BaZrO_3$, NiX—$Ba_2(YSn)O_{5.5}$, NiX—$Ba_3(CaNb_2)O_9$), where X is one or more of Au, Fe, Zn, Mo, Pt, and Pb. In some such embodiments, the positive electrode 108 comprises Ni—BZCYYb or NiAu—BZCYYb. As another non-limiting example, if the proton-conducting membrane 110 comprises a solid acid material (e.g., a doped $CsH_2PO_4$, an undoped $CsH_2PO_4$) having an operational temperature within a range of from about 200° C. to about 400° C., the positive electrode 108 may comprise a material (e.g., an alloy material, a non-alloy material) including at least one catalyst (e.g., at least one metal catalyst, such as Ni) formulated to promote the production of $C_2H_4$, $H^+$, and $e^-$ from $C_2H_6$ in accordance with Equation (1) above, and, optionally, at least one additional catalyst (e.g., at least one additional metal catalyst, such as one or more of Au, Fe, Zn, Mo, Pt, and Pb) formulated to promote the synthesis of higher hydrocarbons from the produced $C_2H_4$ in accordance with Equation (2) above. The positive electrode 108 may, for example, comprise one or more of elemental Ni; an Ni alloy; and an NiX alloy, where X is one or more of Au, Fe, Zn, Mo, Pt, and Pb. In some such embodiments, the positive electrode 108 comprises an NiAu alloy. As a further non-limiting example, if the proton-conducting membrane 110 comprises a PBI material (e.g., a doped PBI) having an operational temperature within a range of from about 150° C. to about 250° C., the positive electrode 108 may comprise a material (e.g., an alloy material, a non-alloy material) including at least one catalyst (e.g., at least one metal catalyst, such as Ni) formulated to promote the production of $C_2H_4$, $H^+$, and $e^-$ from $C_2H_6$ in accordance with Equation (1) above, and, optionally, at least one additional catalyst (e.g., at least one additional metal catalyst, such as one or more of Au, Fe, Zn, Mo, Pt, and Pb.) formulated to promote the synthesis of higher hydrocarbons from the produced $C_2H_4$ in accordance with Equation (2) above. The positive electrode 108 may, for example, comprise one or more of elemental Ni; an Ni alloy; and an NiX alloy, where X is one or more of Au, Fe, Zn, Mo, Pt, and Pb. In some such embodiments, the positive electrode 108 comprises an NiAu alloy.

In embodiments wherein the $C_2H_6$ activation system 100 is free of the $CO_2$ source 103 (e.g., the $CO_2$ source 103 is omitted from the $C_2H_6$ activation system 100), the material of the negative electrode 112 may be formulated to promote the production of $H_{2(g)}$ from $H^+$ and $e^-$ in accordance with Equation (3) above. For example, the material of the negative electrode 112 may comprise a catalyst-doped material including at least one catalyst thereon, thereover, and/or therein that accelerates reaction rates at the negative electrode 112 to produce $H_{2(g)}$ from $H^+$ and $e^-$ in accordance with Equation (3) above. The catalyst(s) may, for example, include at least one metal catalyst, such as one or more of Ni, and platinum (Pt). The catalyst-doped material of the negative electrode 112 may include particles of the catalyst(s), such as nano-sized particles (e.g., nano-sized elemental particles, nano-sized alloy particles, and/or nano-sized composite particles) of the catalyst(s). The catalyst-doped material of the negative electrode 112 may exhibit any amount (e.g., concentration) and distribution of the catalyst(s) facilitating desired hydrogen evolution reaction rates at the negative electrode 112. As another example, the material of the negative electrode 112 may comprise a non-catalyst-doped material substantially free of catalytic particles thereon, thereover, and/or therein, but that still promotes the production of $H_{2(g)}$ from $H^+$ and $e^-$ at the negative electrode 112 in accordance with Equation (3) above.

As a non-limiting example, if the proton-conducting membrane 110 comprises a perovskite material (e.g., a BZCYYb, a BSNYYb, a doped $BaCeO_3$, a doped $BaZrO_3$, $Ba_2(YSn)O_{5.5}$, $Ba_3(CaNb_2)O_9$, etc.) having an operational temperature within a range of from about 350° C. to about 650° C., the negative electrode 112 may comprise a compatible perovskite material, such as cermet material including at least one perovskite (e.g., a BZCYYb, a BSNYYb, a doped $BaCeO_3$, a doped $BaZrO_3$, $Ba_2(YSn)O_{5.5}$, $Ba_3(CaNb_2)O_9$, etc.) and at least one catalyst (e.g., at least one metal catalyst, such as Ni) formulated to promote the production of $H_{2(g)}$ from $H^+$ and $e^-$ in accordance with Equation (3) above, or a double perovskite material (e.g., $PrBa_{0.5}Sr_{0.5}Co_{1.5}Fe_{0.5}O_{5+\delta}$ (PBSCF), wherein δ is the oxygen deficit). The negative electrode 112 may, for example, comprise one or more of a Ni/perovskite cermet (Ni-perovskite) material (e.g., Ni—BZCYYb, Ni—BSNYYb, Ni—BaCeO_3, Ni—BaZrO_3, Ni—Ba_2(YSn)O_{5.5}, Ni—Ba_3(CaNb_2)O_9); and PBSCF. In some such embodiments, the negative electrode 112 comprises Ni—BZCYYb or PBSCF. As another non-limiting example, if the proton-conducting membrane 110 comprises a solid acid material (e.g., a doped $CsH_2PO_4$, an undoped $CsH_2PO_4$) having an operational temperature within a range of from about 200° C. to about 400° C., the negative electrode 112 may comprise a cermet material comprising at least one solid acid (e.g., $CsH_2PO_4$) compatible with the solid acid material of the proton-conducting membrane 110 and at least one catalyst (e.g., at least one metal catalyst, such as one or more of Pt, Pd, and Ru) formulated to promote the production of $H_{2(g)}$ from $H^+$ and $e^-$ in accordance with Equation (3) above, or may comprise a carbon structure having least one catalyst (e.g., at least one metal catalyst, such as one or more of Pt, Pd, and Ru) thereon formulated to promote the production of $H_{2(g)}$ from $H^+$ and $e^-$ in accordance with Equation (3) above. In some such embodiments, the negative electrode 112 comprises a Pt/solid acid cermet (e.g., Pt—$CsH_2PO_4$). As a further non-limiting example, if the proton-conducting membrane 110 comprises a PBI material (e.g., a doped PBI) having an operational temperature within a range of from about 150° C. to about 250° C., the negative electrode 112 may comprise a material (e.g., an alloy material, a non-alloy material) including at least one catalyst (e.g., at least one metal catalyst, such as one or more of Ni and Pt) formulated to promote the production of $H_{2(g)}$ from $H^+$ and $e^-$ in accordance with Equation (3) above. In some such embodiments, the negative electrode 112 comprises one or more of Ni, Pt, a Ni alloy, and a Pt alloy.

In embodiments wherein the $C_2H_6$ activation system 100 includes the $CO_2$ source 103, the material of the negative electrode 112 may be formulated to promote the production of one or more protonation products from $H^+$, $e^-$, and one or more of $CO_2$, $CO_2$ protonation products (e.g., protonation products formed through reactions between $H^+$, $e^-$, and one or more of $CO_2$ and other $CO_2$ protonation products), and reaction products of $CO_2$, $CO_2$ protonation products, and other molecules (e.g., through one or more of Equations (4) through (6) above). For example, the material of the negative electrode 112 may comprise a catalyst-doped material including at least one catalyst thereon, thereover, and/or therein that accelerates reaction rates at the negative electrode 112 to produce protonation products in accordance with one or more of Equations (4) through (6) above. The catalyst(s) may, for example, include at least one metal catalyst, such as one or more of Ni, Pt, copper (Cu), zinc (Zn), and molybdenum (Mo). The catalyst-doped material of the negative electrode 112 may include particles of the catalyst(s), such as nano-sized particles (e.g., nano-sized elemental particles, nano-sized alloy particles, and/or nano-sized composite particles) of the catalyst(s). The catalyst-doped material of the negative electrode 112 may exhibit any amount (e.g., concentration) and distribution of the catalyst(s) facilitating desired electrochemical protonation reaction rates at the negative electrode 112.

As a non-limiting example, if the proton-conducting membrane 110 comprises a perovskite material (e.g., a BZCYYb, a BSNYYb, a doped $BaCeO_3$, a doped $BaZrO_3$, $Ba_2(YSn)O_{5.5}$, $Ba_3(CaNb_2)O_9$, etc.) having an operational temperature within a range of from about 350° C. to about 650° C., the negative electrode 112 may comprise a compatible perovskite material, such as cermet material including at least one perovskite (e.g., a BZCYYb, a BSNYYb, a doped $BaCeO_3$, a doped $BaZrO_3$, $Ba_2(YSn)O_{5.5}$, $Ba_3(CaNb_2)O_9$, etc.) and at least one catalyst (e.g., at least one metal catalyst, such as Ni) formulated to promote the production of one or more protonation products from $H^+$, $e^-$, and one or more of $CO_2$, $CO_2$ protonation products, and reaction products of $CO_2$, $CO_2$ protonation products, and other molecules (e.g., through one or more of Equations (4) through (6) above), or a perovskite material (e.g., a cermet material including at least one perovskite) coated with a catalytic material (e.g., Cu; Zn; a Cu alloy, a Zn alloy, a CuZn alloy, a CuMo alloy, and/or a ZnMo alloy) formulated to promote the production of one or more protonation products from $H^+$, $e^-$, and one or more of $CO_2$, $CO_2$ protonation products, and reaction products of $CO_2$, $CO_2$ protonation products, and other molecules (e.g., through one or more of Equations (4) through (6) above). The negative electrode 112 may, for example, comprise one or more of a Ni/perovskite cermet (Ni-perovskite) material (e.g., Ni—

BZCYYb, Ni—BSNYYb, Ni—BaCeO$_3$, Ni—BaZrO$_3$, Ni—Ba$_2$(YSn)O$_{5.5}$, Ni—Ba$_3$(CaNb$_2$)O$_9$); a Ni/perovskite cermet coated with Cu; a Ni/perovskite cermet coated with Zn; a Ni/perovskite cermet coated with a Cu alloy; a Ni/perovskite cermet coated with a Zn alloy; a Ni/perovskite cermet coated with a CuZn alloy; a Ni/perovskite cermet coated with a CuMo alloy; and/or a Ni/perovskite cermet coated with a ZnMo alloy. In some such embodiments, the negative electrode 112 comprises Ni—BZCYYb. As another non-limiting example, if the proton-conducting membrane 110 comprises a solid acid material (e.g., a doped CsH$_2$PO$_4$, an undoped CsH$_2$PO$_4$) having an operational temperature within a range of from about 200° C. to about 400° C., the negative electrode 112 may comprise a cermet material comprising at least one solid acid (e.g., CsH$_2$PO$_4$) compatible with the solid acid material of the proton-conducting membrane 110 and at least one catalyst (e.g., at least one metal catalyst, such as one or more of Ni, Cu, Zn, and Pt) formulated to promote the production of one or more protonation products from H$^+$, e$^-$, and one or more of CO$_2$, CO$_2$ protonation products, and reaction products of CO$_2$, CO$_2$ protonation products, and other molecules (e.g., through one or more of Equations (4) through (6) above). In some such embodiments, the negative electrode 112 comprises a Pt/solid acid cermet (e.g., Pt—CsH$_2$PO$_4$). As a further non-limiting example, if the proton-conducting membrane 110 comprises a PBI material (e.g., a doped PBI) having an operational temperature within a range of from about 150° C. to about 250° C., the negative electrode 112 may comprise a material (e.g., an alloy material, a non-alloy material) including at least one catalyst (e.g., at least one metal catalyst, such as one or more of Ni, Cu, Zn, and Pt) formulated to promote the production of one or more protonation products from H$^+$, e$^-$, and one or more of CO$_2$, CO$_2$ protonation products, and reaction products of CO$_2$, CO$_2$ protonation products, and other molecules (e.g., through one or more of Equations (4) through (6) above). In some such embodiments, the negative electrode 112 comprises one or more of Ni, Cu, Zn, Pt, a Ni alloy, a Cu alloy, a Zn alloy, and a Pt alloy.

The positive electrode 108 and the negative electrode 112 may individually exhibit any desired dimensions (e.g., length, width, thickness) and any desired shape (e.g., a cubic shape, cuboidal shape, a tubular shape, a tubular spiral shape, a spherical shape, a semi-spherical shape, a cylindrical shape, a semi-cylindrical shape, a conical shape, a triangular prismatic shape, a truncated version of one or more of the foregoing, and irregular shape). The dimensions and the shapes of the positive electrode 108 and the negative electrode 112 may be selected relative to the dimensions and the shape of the proton-conducting membrane 110 such that the proton-conducting membrane 110 substantially intervenes between opposing surfaces of the positive electrode 108 and the negative electrode 112. Thicknesses of the positive electrode 108 and the negative electrode 112 may individually be within a range of from about 10 µm to about 1000 µm.

The electrochemical cell 106, including the positive electrode 108, the proton-conducting membrane 110, and the negative electrode 112 thereof, may be formed through conventional processes (e.g., rolling processes, milling processes, shaping processes, pressing processes, consolidation processes, etc.), which are not described in detail herein. The electrochemical cell 106 may be mono-faced or bi-faced and may have a prismatic, folded, wound, cylindrical, or jelly rolled configuration. The electrochemical cell 106 may be placed within the housing structure 114 to form the electrochemical apparatus 104, and may be electrically connected to the power source 116.

Although the electrochemical apparatus 104 is depicted as including a single (i.e., only one) electrochemical cell 106 in FIG. 1, the electrochemical apparatus 104 may include any number of electrochemical cells 106. Put another way, the electrochemical apparatus 104 may include a single (e.g., only one) electrochemical cell 106, or may include multiple (e.g., more than one) electrochemical cells 106. If the electrochemical apparatus 104 includes multiple electrochemical cells 106, each of the electrochemical cells 106 may be substantially the same (e.g., exhibit substantially the same components, component sizes, component shapes, component material compositions, component material distributions, component positions, component orientations, etc.) and may be operated under substantially the same conditions (e.g., substantially the same temperatures, pressures, flow rates, etc.), or at least one of the electrochemical cells 106 may be different (e.g., exhibit one or more of different components, different component sizes, different component shapes, different component material compositions, different component material distributions, different component positions, different component orientations, etc.) than at least one other of the electrochemical cells 106 and/or may be operated under different conditions (e.g., different temperatures, different pressures, different flow rates, etc.) than at least one other of the electrochemical cells 106. By way of non-limiting example, one of the electrochemical cells 106 may be configured for and operated under a different temperature (e.g., different operating temperature resulting from a different material composition of one or more components thereof, such as a different material composition of the proton-conducting membrane 110 thereof) than at least one other of the electrochemical cells 106. In some embodiments, two or more electrochemical cells 106 are provided in parallel with one another within the housing structure 114 of the electrochemical apparatus 104, and individually produce a portion of the hydrocarbon product(s) directed out of the electrochemical apparatus 104 as the hydrocarbon product stream 124 and a portion of the protonation products (e.g., H$_{2(g)}$, CO$_2$ protonation products) directed out of the electrochemical apparatus 104 as the protonation product stream 126.

In addition, although the C$_2$H$_6$ activation system 100 is depicted as including a single (i.e., only one) electrochemical apparatus 104 in FIG. 1, the C$_2$H$_6$ activation system 100 may include any number of electrochemical apparatuses 104. Put another way, the C$_2$H$_6$ activation system 100 may include a single (e.g., only one) electrochemical apparatus 104, or may include multiple (e.g., more than one) electrochemical apparatuses 104. If the C$_2$H$_6$ activation system 100 includes multiple electrochemical apparatuses 104, each of the electrochemical apparatuses 104 may be substantially the same (e.g., exhibit substantially the same components, component sizes, component shapes, component material compositions, component material distributions, component positions, component orientations, etc.) and may be operated under substantially the same conditions (e.g., substantially the same temperatures, pressures, flow rates, etc.), or at least one of the electrochemical apparatuses 104 may be different (e.g., exhibit one or more of different components, different component sizes, different component shapes, different component material compositions, different component material distributions, different component positions, different component orientations, etc.) than at least one other of the electrochemical apparatuses 104 and/or may be operated under different conditions (e.g., different temperatures, different pressures, different flow rates, etc.) than at least one other of the electrochemical apparatuses 104. By way of non-limiting example, one of the electrochemical apparatuses 104 may be configured for and operated under a different temperature (e.g., a different operating temperature resulting from a different material composition of one or more components of an electrochemical cell 106 thereof, such as a different material composition of the proton-conducting membrane 110 thereof) than at least one other of the electrochemical apparatuses 104. In some embodiments, two or more electrochemical apparatuses 104 are provided in parallel with one another. Each of the two or more electrochemical apparatuses 104 may individually receive a $C_2H_6$ stream 120 and may individually form a hydrocarbon product stream 124 and a protonation product stream 126.

Still referring to FIG. 1, the hydrocarbon product stream 124 and the protonation product stream 126 exiting the electrochemical apparatus 104 may individually be utilized or disposed of as desired. In some embodiments, the hydrocarbon product stream 124 and the protonation product stream 126 are individually delivered into one or more storage vessels for subsequent use, as desired. In additional embodiments, at least a portion of one or more of the hydrocarbon product stream 124 and the protonation product stream 126 may be utilized (e.g., combusted) to heat one or more components (e.g., the heating apparatus 118 (if present); the electrochemical apparatus 104; etc.) and/or streams (e.g., the $C_2H_6$ stream 120, the $CO_2$ stream 125 (if any)) of the $C_2H_6$ activation system 100. By way of non-limiting example, as shown in FIG. 1, if the heating apparatus 118 (if present) is a combustion-based apparatus, at least a portion of one or more of the hydrocarbon product stream 124 and the protonation product stream 126 may be directed into the heating apparatus 118 and undergo an combustion reaction to efficiently heat one or more of the $C_2H_6$ stream 120 entering the electrochemical apparatus 104, the $CO_2$ stream 125 (if any) entering the electrochemical apparatus 104, and at least a portion of the electrochemical apparatus 104. Utilizing the hydrocarbon product stream 124 and/or the protonation product stream 126 as described above may reduce the electrical power requirements of the $C_2H_6$ activation system 100 by enabling the utilization of direct thermal energy.

Thermal energy input into (e.g., through the heating apparatus 118 (if present)) and/or generated by the electrochemical apparatus 104 may also be used to heat one or more other components and/or streams (e.g., the $C_2H_6$ stream 120, the $CO_2$ stream 125 (if any)) of the $C_2H_6$ activation system 100. By way of non-limiting example, the hydrocarbon product stream 124 and/or the protonation product stream 126 exiting the electrochemical apparatus 104 may be directed into a heat exchanger configured and operated to facilitate heat exchange between the hydrocarbon product stream 124 and/or the protonation product stream 126 of the $C_2H_6$ activation system 100 and one or more other relatively cooler streams (e.g., the $C_2H_6$ stream 120, the $CO_2$ stream 125 (if any)) of the $C_2H_6$ activation system 100 to transfer heat from the hydrocarbon product stream 124 and/or the protonation product stream 126 to the relatively cooler stream(s) to facilitate the recovery of the thermal energy input into and generated within the electrochemical apparatus 104. The recovered thermal energy may increase process efficiency and/or reduce operational costs without having to react (e.g., combust) higher hydrocarbon products of the hydrocarbon product stream 124 and/or protonation products of the protonation product stream 126.

The methods, systems (e.g., the $C_2H_6$ activation system 100), and apparatuses (e.g., the electrochemical apparatus 104, including the electrochemical cell 106 thereof) of the disclosure facilitate the simple and efficient co-production of hydrocarbons (e.g., ethylene, butylene, gasoline, diesel, etc.) and protonation products (e.g., $H_{2(g)}$, $CO_2$ protonation products) from $C_2H_6$ at intermediate temperatures, such as temperatures within a range of from about 150° C. to about 650° C. The methods, systems, and apparatuses of the disclosure may reduce one or more of the time (e.g., processing steps), costs (e.g., material costs), and energy (e.g., thermal energy, electrical energy, etc.) required to produce hydrocarbons from $C_2H_6$ relative to conventional methods, systems, and apparatuses of producing higher hydrocarbons from $C_2H_6$. The methods, systems, and apparatuses of the disclosure may be more efficient, durable, and reliable than conventional methods, conventional systems, and conventional apparatuses of producing hydrocarbons and protonation products (e.g., $H_{2(g)}$, $CO_2$ protonation products).

Additional non-limiting examples of embodiments of this disclosure are set forth below.

Embodiment 1: A method of forming a hydrocarbon product comprises introducing $C_2H_6$ to a positive electrode of an electrochemical cell comprising the positive electrode, a negative electrode, and a proton-conducting membrane between the positive electrode and the negative electrode. The proton-conducting membrane comprises an electrolyte material having an ionic conductivity greater than or equal to about $10^{-2}$ S/cm at one or more temperatures within a range of from about 150° C. to about 650° C. A potential difference is applied between the positive electrode and the negative electrode of the electrochemical cell.

Embodiment 2: The method of Embodiment 1, further comprising selecting the positive electrode of the electrochemical cell to comprise at least one catalyst formulated to accelerate reaction rates to produce $C_2H_4$, $H^+$, and $e^-$ from $C_2H_6$.

Embodiment 3: The method of Embodiment 2, further comprising selecting the positive electrode of the electrochemical cell to comprise at least one additional catalyst formulated to accelerate reaction rates to synthesize higher hydrocarbons from the produced $C_2H_4$.

Embodiment 4: The method of Embodiment 1, further comprising selecting the positive electrode of the electrochemical cell to comprise at least one metal formulated to accelerate the production of $C_2H_4$, $H^+$, and $e^-$, and at least one additional metal formulated to accelerate the synthesis of higher hydrocarbons from the produced $C_2H_4$.

Embodiment 5: The method of Embodiment 4, wherein selecting the positive electrode to comprise at least one metal and at least one additional metal comprises selecting the positive electrode to comprise elemental particles of the at least one metal and additional elemental particles of the at least one additional metal discrete from the elemental particles of the at least one metal.

Embodiment 6: The method of Embodiment 4, wherein selecting the positive electrode to comprise at least one metal and at least one additional metal comprises selecting the positive electrode to comprise alloy particles individually comprising an alloy of the at least one metal and the at least one additional metal.

Embodiment 7: The method of Embodiment 4, wherein selecting the positive electrode to comprise at least one metal and at least one additional metal comprises selecting the positive electrode to comprise composite particles individually comprising a core of one of the at least one metal and the at least one additional metal, and a shell of the other of the at least one metal and the at least one additional metal partially coating the core.

Embodiment 8: The method of any one of Embodiments 4 through 7, wherein selecting the positive electrode of the electrochemical cell to comprise to comprise at least one metal and at least one additional metal comprises selecting the positive electrode to comprise Ni and one or more of Au, Fe, Zn, Mo, Pt, and Pb.

Embodiment 9: The method of any one of Embodiments 1 through 8, further comprising selecting the negative electrode of the electrochemical cell to comprise a material formulated to accelerate reaction rates to produce $H_{2(g)}$ from $H^+$ and $e^-$.

Embodiment 10: The method of any one of Embodiments 1 through 8, further comprising introducing $CO_2$ to the negative electrode of the electrolysis cell; and protonating the $CO_2$ at the negative electrode during the application of the potential difference between the positive electrode and the negative electrode of the electrochemical cell.

Embodiment 11: The method of Embodiment 10, further comprising selecting the negative electrode of the electrochemical cell to comprise at least one catalyst formulated to accelerate reaction rates to synthesize one or more products through the protonation of $CO_2$.

Embodiment 12: The method of any one of Embodiments 1 through 11, further comprising selecting the proton-conducting membrane of the electrochemical cell to comprise at least one perovskite material having a $H^+$ conductivity greater than or equal to about $10^{-2}$ S/cm at one or more temperatures within a range of from about 350° C. to about 650° C.

Embodiment 13: The method of Embodiment 12, wherein selecting the proton-conducting membrane of the electrochemical cell to comprise at least one perovskite material comprises selecting the at least one perovskite material to comprise one or more of BZCYYb, BSNYYb, BCY, BZY, $Ba_2(YSn)O_{5.5}$, and $Ba_3(CaNb_2)O_9$.

Embodiment 14: The method of Embodiment 12, wherein selecting the proton-conducting membrane of the electrochemical cell to comprise at least one perovskite material comprises selecting the proton-conducting membrane a stack of at least two different perovskite materials each individually having a $H^+$ conductivity greater than or equal to about $10^{-2}$ S/cm at one or more temperatures within a range of from about 350° C. to about 650° C.

Embodiment 15: The method of any of Embodiments 12 through 14, further comprising selecting the positive electrode to comprise a first perovskite material comprising a cermet material including at least one perovskite and one or more of Ni, Au, Fe, Zn, Mo, Pt, and Pb; and selecting the negative electrode to comprise a second perovskite material comprising one or more of a Ni/perovskite cermet, Ni/perovskite cermet coated with a Cu-containing material, Ni/perovskite cermet coated with a Zn-containing material, and a double perovskite.

Embodiment 16: The method of any one of Embodiments 1 through 11, further comprising selecting the proton-conducting membrane of the electrochemical cell to comprise an electrolyte material selected from the group consisting of a perovskite material having a $H^+$ conductivity greater than about $10^{-2}$ S/cm at one or more temperatures within a range of from about 350° C. to about 650° C., a solid acid material having a $H^+$ conductivity greater than or equal to about $10^{-2}$ S/cm at one or more temperatures within a range of from about 200° C. to about 400° C., and a PBI material having a $H^+$ conductivity greater than or equal to about $10^{-2}$ S/cm at one or more temperatures within a range of from about 150° C. to about 200° C.

Embodiment 17: A $C_2H_6$ activation system comprises a source of $C_2H_6$ and an electrochemical apparatus in fluid communication with the source of $C_2H_6$. The electrochemical apparatus comprises a housing structure configured and positioned to receive a $C_2H_6$ stream from the source of $C_2H_6$, and an electrochemical cell within an internal chamber of the housing structure. The electrochemical cell comprises a positive electrode, a negative electrode, and a proton-conducting membrane between the positive electrode and the negative electrode. The positive electrode is formulated to accelerate reaction rates to produce $C_2H_4$, $H^+$, and $e^-$ from $C_2H_6$. The negative electrode is formulated to accelerate reaction rates to synthesize a protonation product using the produced $H^+$. The proton-conducting membrane comprises an electrolyte material having an ionic conductivity greater than or equal to about $10^{-2}$ S/cm at one or more temperatures within a range of from about 150° C. to about 650° C.

Embodiment 18: The $C_2H_6$ activation system of Embodiment 17, wherein the electrolyte material of the proton-conducting membrane is selected from the group consisting of a perovskite material having a $H^+$ conductivity greater than about $10^{-2}$ S/cm at one or more temperatures within a range of from about 350° C. to about 650° C., a solid acid material having a $H^+$ conductivity greater than or equal to about $10^{-2}$ S/cm at one or more temperatures within a range of from about 200° C. to about 400° C., and a PBI material having a $H^+$ conductivity greater than or equal to about $10^{-2}$ S/cm at one or more temperatures within a range of from about 150° C. to about 200° C.

Embodiment 19: The $C_2H_6$ activation system of Embodiment 17 or Embodiment 18, wherein the positive electrode comprises Ni.

Embodiment 20: The $C_2H_6$ activation system of any one of Embodiments 17 through 19, wherein the positive electrode is further formulated to accelerate reaction rates to synthesize at least one hydrocarbon product from the produced $C_2H_4$ and comprises Ni and one or more of Au, Fe, Zn, Mo, Pt, and Pb.

Embodiment 21: The $C_2H_6$ activation system of any one of Embodiments 17 through 20, wherein the positive electrode comprises an alloy of Ni and one or more of Au, Fe, Zn, Mo, Pt, and Pb.

Embodiment 22: The $C_2H_6$ activation system of any one of Embodiments 17 through 20, wherein the catalyst material of positive electrode comprises one or more of composite particles individually comprising a core of Ni and a shell of one or more of Au, Fe, Zn, Mo, Pt, and Pb partially coating the core, and additional composite particles individually comprising an additional core of one or more of Au, Fe, Zn, Mo, Pt, and Pb and an additional shell of Ni.

Embodiment 23: The $C_2H_6$ activation system of any one of Embodiments 17 through 22, wherein the negative electrode is formulated to accelerate reaction rates to synthesize $H_{2(g)}$ from $H^+$ and $e^-$.

Embodiment 24: The $C_2H_6$ activation system of any one of Embodiments 17 through 22, further comprising a source of $CO_2$ in fluid communication with the negative electrode of the electrochemical cell, the negative electrode formulated to accelerate reaction rates to synthesize a protonation product from $CO_2$, $H^+$, and $e^-$.

Embodiment 25: An electrochemical cell comprises a positive electrode, a negative electrode, and a proton-conducting membrane between the positive electrode and the negative electrode. The positive electrode comprises a first catalyst material formulated to accelerate to $C_2H_6$ deprotonation reaction rates to produce $C_2H_4$, $H^+$, and $e^-$, from $C_2H_6$, and to accelerate ethyl coupling reaction rates to synthesize at least one hydrocarbon product from the produced $C_2H_4$. The negative electrode comprises a second catalyst material formulated to accelerate reaction rates to synthesize a protonation product using the produced $H^+$. The proton-conducting membrane comprises an electrolyte material having an ionic conductivity greater than or equal to about $10^{-2}$ S/cm at one or more temperatures within a range of from about 150° C. to about 650° C.

The following examples serve to explain embodiments of the disclosure in more detail. These examples are not to be construed as being exhaustive or exclusive as to the scope of the disclosure.

EXAMPLES

Example 1

Figure 3:
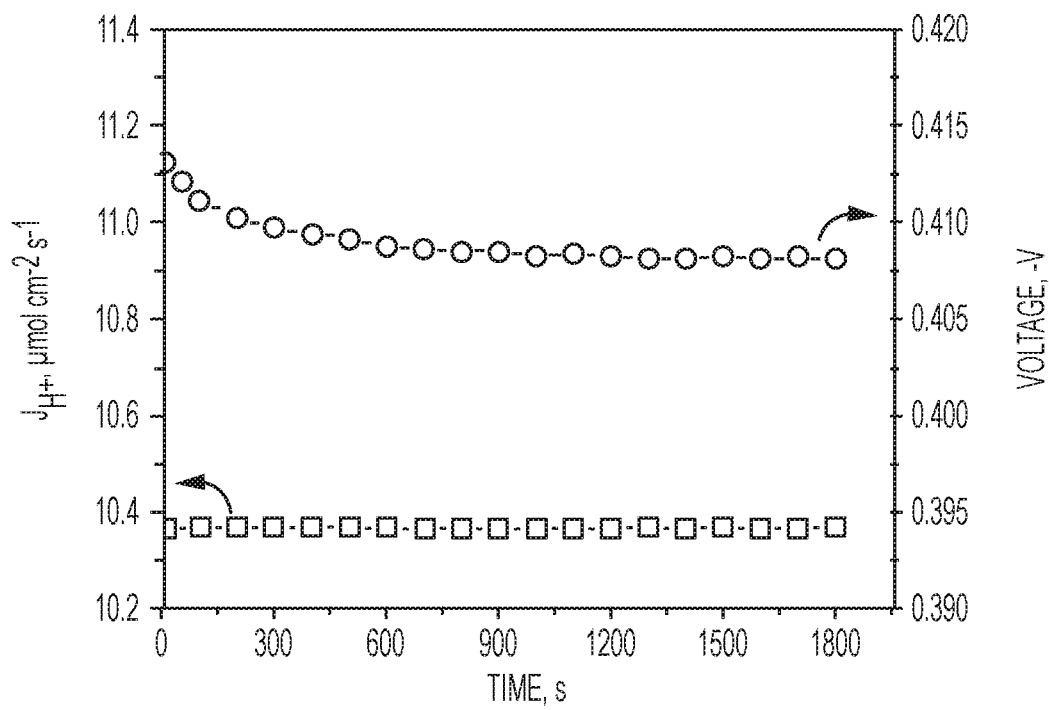
FIG. 3 is a graphical representation of the results described in Example 1.

Electrochemical non-oxidative deprotonation (NDP) of $C_2H_6$ was performed at temperatures of 400° and 500° C. using an electrochemical cell exhibiting the general configuration of the electrochemical cell 106 shown in FIG. 1, including a positive electrode (e.g., the positive electrode 108) comprising NiO—BZCYYb, a proton-conducting membrane (e.g., the proton-conducting membrane 110) comprising BZCYYb, and a negative electrode (e.g., the negative electrode 112) comprising PBSCF. As shown in FIG. 3, a constant current density of 1 A/cm² was applied to the electrochemical cell as 10% $C_2H_6$ in argon (Ar) was introduced to the positive electrode (anode). This corresponded to a proton flux of 10.37 µmol/cm²s or a hydrogen production rate of 0.448 mol/cm² per day, which was confirmed by gas chromatography (GC) analysis on the negative electrode (cathode) side. At 400° C., the Gibbs free energy for the reaction $C_2H_6 \leftrightarrows C_2H_4 + H_2$ is 51.7 kJ/mol, which is equivalent to a thermodynamic potential of −0.268 V. The recorded voltage generally reached equilibrium in 20 minutes (min), and a relatively small value (−0.408 V), was obtained upon equilibrium. The overpotential was thus calculated as only 140 mV. According to the conductivity of BZCYYb, the Ohmic overpotential associated with the electrolyte was 83 mV while the overpotential contributed by positive and negative electrode reactions was 57 mV. The low overpotential demonstrated successful assembly of the electrochemical cell and small electrical energy consumption.

Example 2

Figure 4:
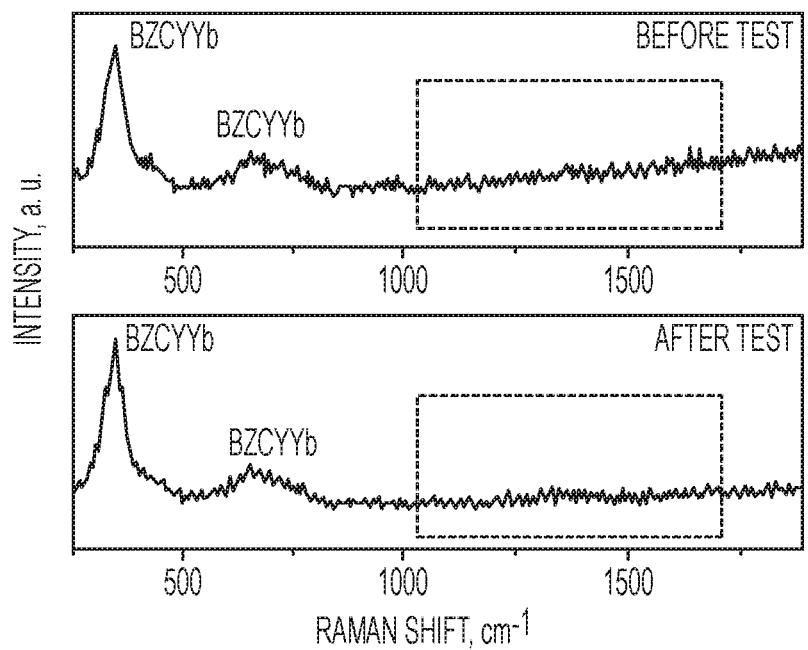
FIG. 4 is a graphical representation of the results described in Example 2.

Online GC analysis was employed to analyze hydrocarbon products synthesized through electrochemical NDP of $C_2H_6$ using the electrochemical cell previously described in Example 1. Potential hydrocarbon products synthesized through the electrochemical NDP of $C_2H_6$ included $C_2H_4$, $CH_4$, and $C_2H_2$. The GC results indicated that the hydrocarbon products were free of both $CH_4$, and $C_2H$. In addition, both ex-situ and in-situ Raman spectroscopic measurements were performed to identify coke formation. FIG. 4 shows the ex-situ Raman spectra of the positive electrode (anode) in the electrochemical cell before and after electrochemical NDP at 400° C. The Raman bands at the low wavenumber region correspond to the vibration bands of BZCYYb. No Raman band of carbonaceous species appeared in the cell after test, as marked in the dashed region. This was further confirmed by in-situ Raman spectroscopy in a predesigned in-situ cell where the cell was exposed to $C_2H_6$ for 45 min with an interval of 90 seconds (s). The results indicate that $C_2H_4$ selectivity facilitated through electrochemical NDP of $C_2H_6$ using the electrochemical cell was close to 100%.

Example 3

Figure 5:
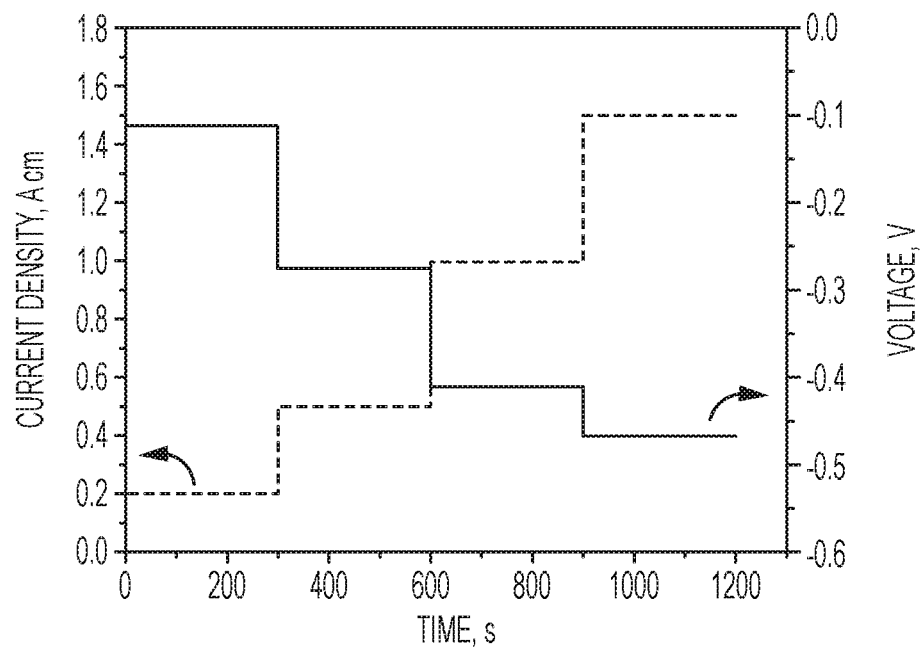
FIG. 5 is a graphical representation of the results described in Example 3.

The relationship between current density and voltage during operation of the electrochemical cell previously described in Example 1 was investigated to determine the effect of input electrical energy on reaction rate. As shown in FIG. 5, voltage was −0.113V, −0.275 V, −0.408 V, and −0.465 V at a current density of 0.2 A/cm², 0.5 A/cm², 1.0 A/cm², and 1.5 A/cm², respectively. The total electrochemical cell resistance, calculated from V/I, tended to decrease with increasing current density.

Example 4

Figure 6:
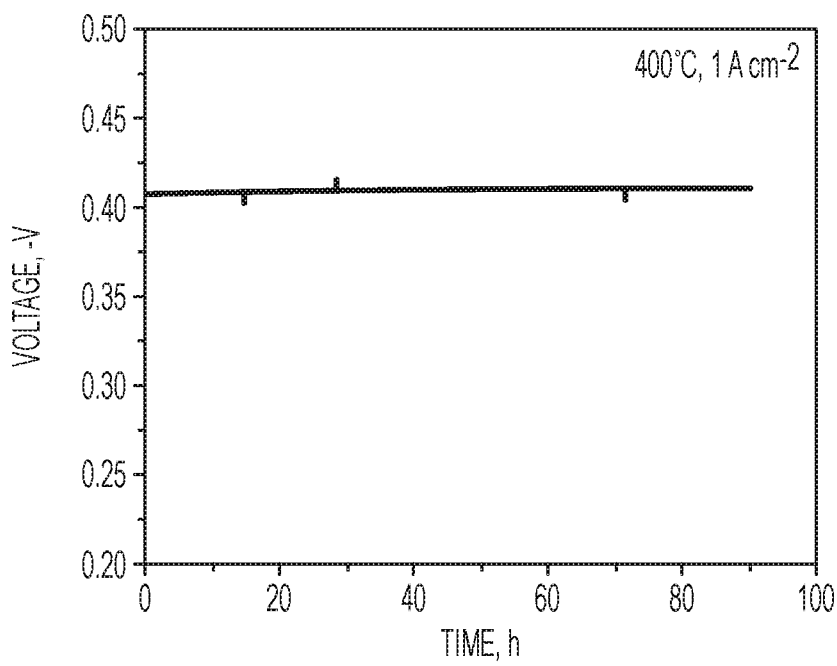
FIG. 6 is a graphical representation of the results described in Example 4.

A long-term stability test was performed to analyze the durability of the electrochemical cell previously described in Example 1, including the materials employed therein. FIG. 6 shows the voltage response at a constant current density of 1 A/cm² with a 10% $C_2H_6$ in Ar for over 90 hours (h). The voltage fluctuated slightly in the range of −0.407 V and −0.413 V, indicating that the electrochemical cell has good durability under the operating conditions thereof. The results were consistent with observed Raman spectroscopy results.

Example 5

Figure 7:
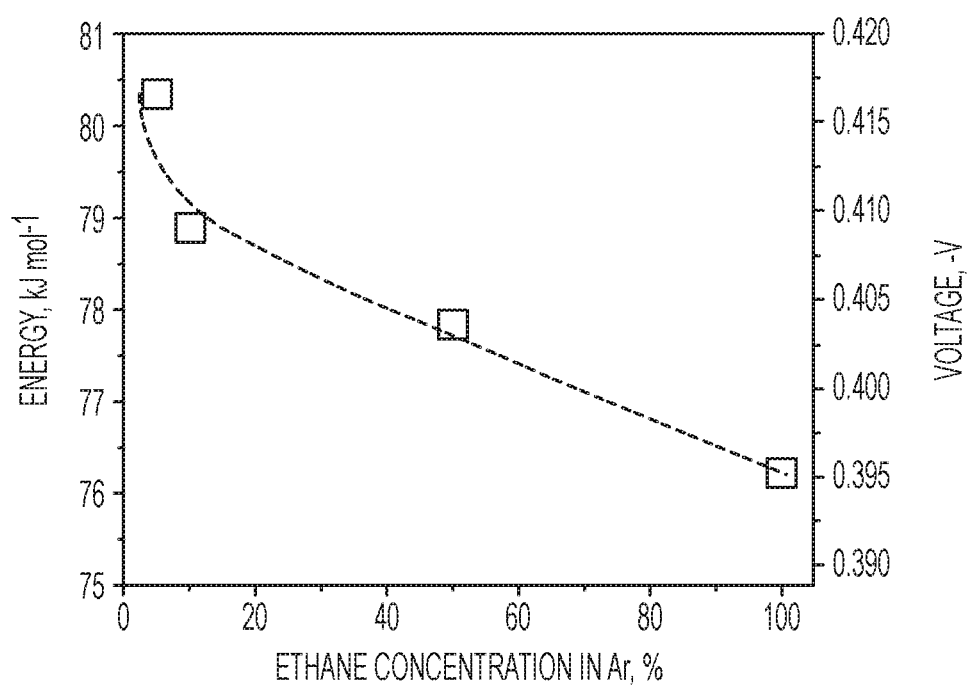
FIG. 7 is a graphical representation of the results described in Example 5.

The relationship between the energy consumption and the $C_2H_6$ concentration for electrochemical NDP of $C_2H_6$ using the electrochemical cell previously described in Example 1 was analyzed and compared against that for conventional $C_2H_6$ thermal-cracking. The energy consumption was converted from recorded electrical voltages under equilibrium. The results of the analysis are depicted in FIG. 7. As shown in FIG. 7, the voltage dropped from −0.417 V to −0.395 V, which corresponded to a decrease in the energy input from 80.3 kJ/mol to 76.2 kJ/mol, when the $C_2H_6$ concentration increased from 5% to 100% while the proton flux was fixed. This indicates that the electrochemical NDP favors higher $C_2H_6$ concentration. In contrast, conventional $C_2H_6$ thermal-cracking favors lower $C_2H_6$ concentration.

While the disclosure is susceptible to various modifications and alternative forms, specific embodiments have been shown by way of example in the drawings and have been described in detail herein. However, the disclosure is not limited to the particular forms disclosed. Rather, the disclosure is to cover all modifications, equivalents, and alternatives falling within the scope of the following appended claims and their legal equivalent. For example, elements and features disclosed in relation to one embodiment may be combined with elements and features disclosed in relation to other embodiments of the disclosure.

What is claimed is:
1. A method of forming a hydrocarbon product and a protonation product, comprising:
   introducing ethane ($C_2H_6$) to a positive electrode of an electrochemical cell comprising:
      the positive electrode, the positive electrode comprising a cermet material comprising:

one or more of a yttrium- and ytterbium-doped barium-zirconate-cerate (BZCYYb) and a yttrium- and ytterbium-doped barium-strontium-niobate (BSNYYb);
nickel; and
at least one catalyst selected from Au, Fe, Zn, Mo, Pt, and Pb;
a negative electrode; and
a proton-conducting membrane between the positive electrode and the negative electrode and comprising one or more of additional BZCYYb and additional BSNYYb, the proton-conducting membrane having an ionic conductivity greater than or equal to about $10^{-2}$ S/cm at one or more temperatures within a range of from about 150° C. to about 650° C.; and
applying a potential difference between the positive electrode and the negative electrode of the electrochemical cell while the $C_2H_6$ interacts with the positive electrode so that hydrogen (H) atoms of the $C_2H_6$ release electrons (e) to produce $C_2H_4$, hydrogen ions ($H^+$), and the $e^-$ through non-oxidative deprotonation of the $C_2H_6$ at the one or more temperatures.

2. The method of claim 1, wherein the at least one catalyst is selected from Au, Zn, Mo, and Pb.

3. The method of claim 1, further comprising selecting the negative electrode of the electrochemical cell to comprise a material formulated to accelerate reaction rates to produce $H_{2(g)}$ from the $H^+$ and the $e^-$.

4. The method of claim 1, further comprising:
introducing $CO_2$ to the negative electrode of the electrolysis cell; and
protonating the $CO_2$ at the negative electrode during the application of the potential difference between the positive electrode and the negative electrode of the electrochemical cell.

5. The method of claim 4, further comprising selecting the negative electrode of the electrochemical cell to comprise at least one catalyst formulated to accelerate reaction rates to synthesize one or more products through the protonation of the $CO_2$.

6. The method of claim 1, further comprising selecting the proton-conducting membrane of the electrochemical cell to have a conductivity greater than or equal to about $10^{-2}$ S/cm at one or more temperatures within a range of from about 350° C. to about 650° C.

7. The method of claim 6, further comprising selecting the negative electrode to comprise a perovskite material comprising one or more of a Ni/perovskite cermet, Ni/perovskite cermet coated with a Cu-containing material, Ni/perovskite cermet coated with a Zn-containing material, and double perovskite.

8. The method of claim 1, further comprising selecting the proton-conducting membrane of the electrochemical cell to comprise the additional BZCYYb.

9. The method of claim 1, further comprising selecting the proton-conducting membrane of the electrochemical cell to comprise the additional BSNYYb.

* * * * *